US 7,615,759 B2

(12) United States Patent
Kimura et al.

(10) Patent No.: US 7,615,759 B2
(45) Date of Patent: Nov. 10, 2009

(54) FLUORESCENCE ANALYSIS APPARATUS

(75) Inventors: Toshihito Kimura, Ashigarakami-gun (JP); Kiyoshi Fujimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 92 days.

(21) Appl. No.: 11/972,724

(22) Filed: Jan. 11, 2008

(65) Prior Publication Data

US 2008/0169430 A1     Jul. 17, 2008

(30) Foreign Application Priority Data

Jan. 11, 2007   (JP)   ............... 2007-003104
Jan. 30, 2007   (JP)   ............... 2007-018874

(51) Int. Cl.
*F21V 9/16* (2006.01)
(52) U.S. Cl. .................................. 250/458.1
(58) Field of Classification Search ............... 250/458.1
See application file for complete search history.

(56) References Cited

U.S. PATENT DOCUMENTS

| 4,582,809 A | 4/1986 | Block et al. |
| 4,703,182 A | 10/1987 | Kroneis et al. |
| 5,703,366 A | 12/1997 | Sting et al. |
| 6,535,283 B1 | 3/2003 | Caniel et al. |
| 6,584,335 B1 | 6/2003 | Haar et al. |
| 2005/0113657 A1 | 5/2005 | Alarcon et al. |
| 2005/0260677 A1 | 11/2005 | Saaski |

FOREIGN PATENT DOCUMENTS

| JP | 10-78390 A | 3/1998 |
| JP | 2004205268 A | 7/2004 |
| JP | 2006-47250 A | 2/2006 |

OTHER PUBLICATIONS

T. Yasuda, Test Method and Evaluation Results of Dynamic Characteristics of Plastic Materials <19>, Plastic, pp. 98-101, vol. 52, No. 8; Aug. 1, 2001.

*Primary Examiner*—David P Porta
*Assistant Examiner*—Kiho Kim
(74) *Attorney, Agent, or Firm*—Sughrue Mion, PLLC

(57) ABSTRACT

After a sensor section has been dipped in a liquid sample, the sensor section is moved into a predetermined atmosphere, which is substantially free from occurrence of absorption or scattering of exciting light and fluorescence. In the state, in which the sensor section has been located in the predetermined atmosphere, exciting light is produced by a light source and is propagated through the interior of the sensor section. The exciting light is radiated out from an outside surface of the sensor section in order to excite a fluorescent substance for indicating the presence of a substance to be analyzed in the liquid sample. Fluorescence, which is produced by the fluorescent substance when the fluorescent substance is excited by the exciting light, is detected by a photodetector.

14 Claims, 12 Drawing Sheets

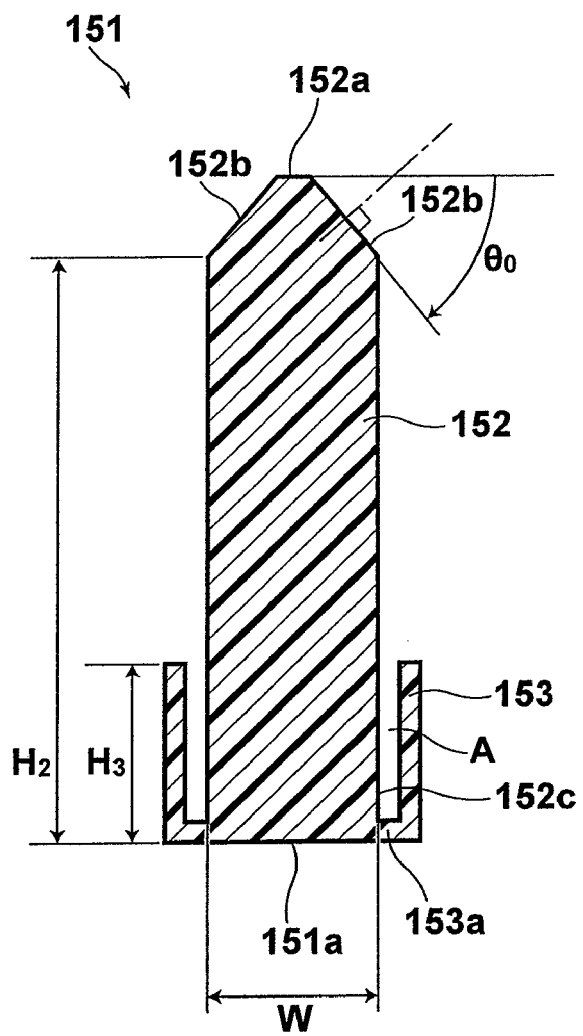
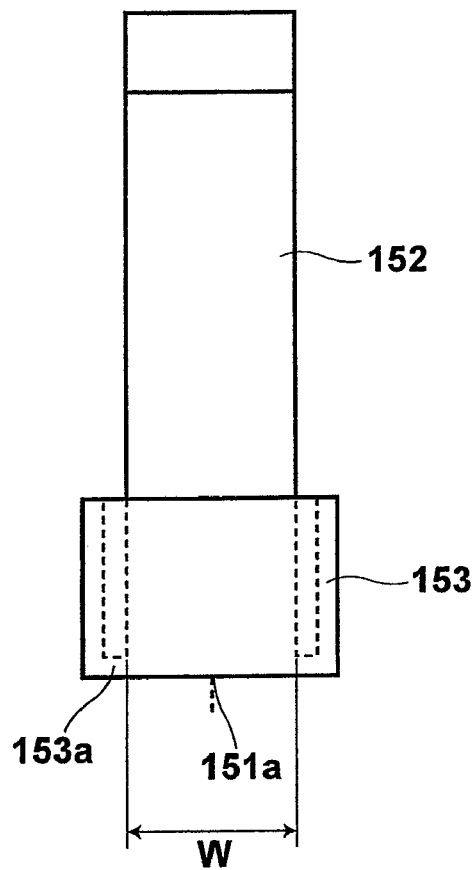

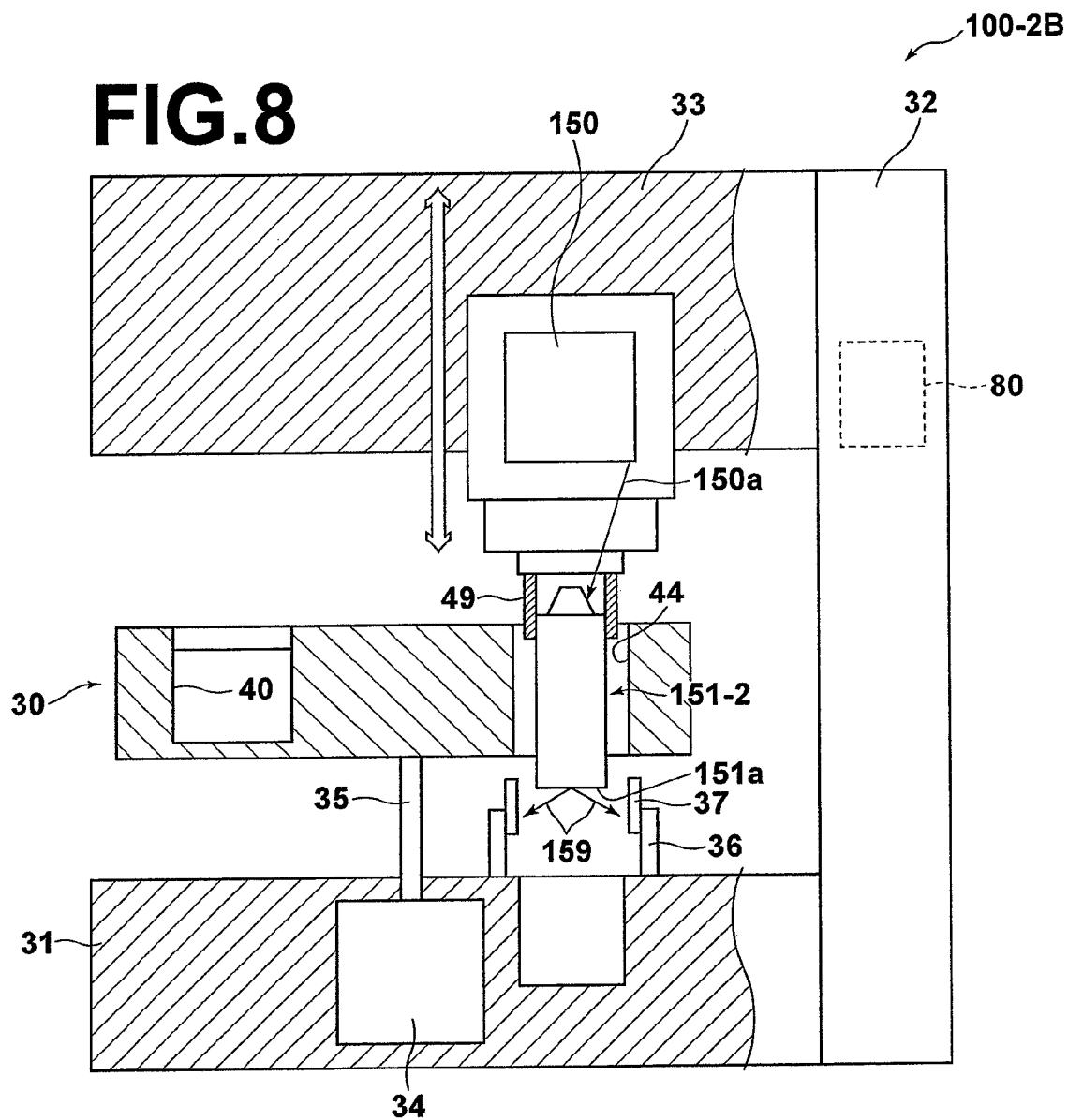

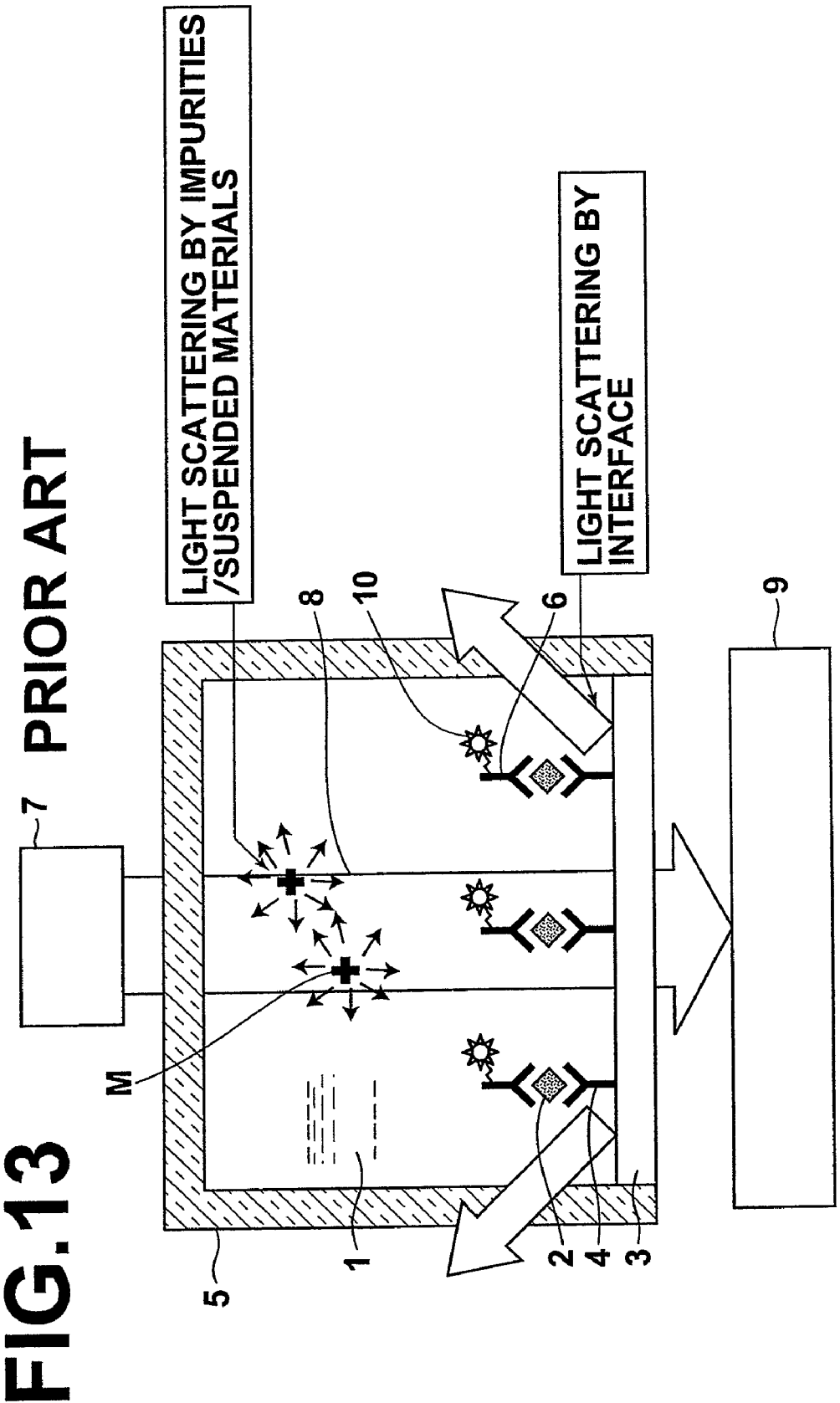

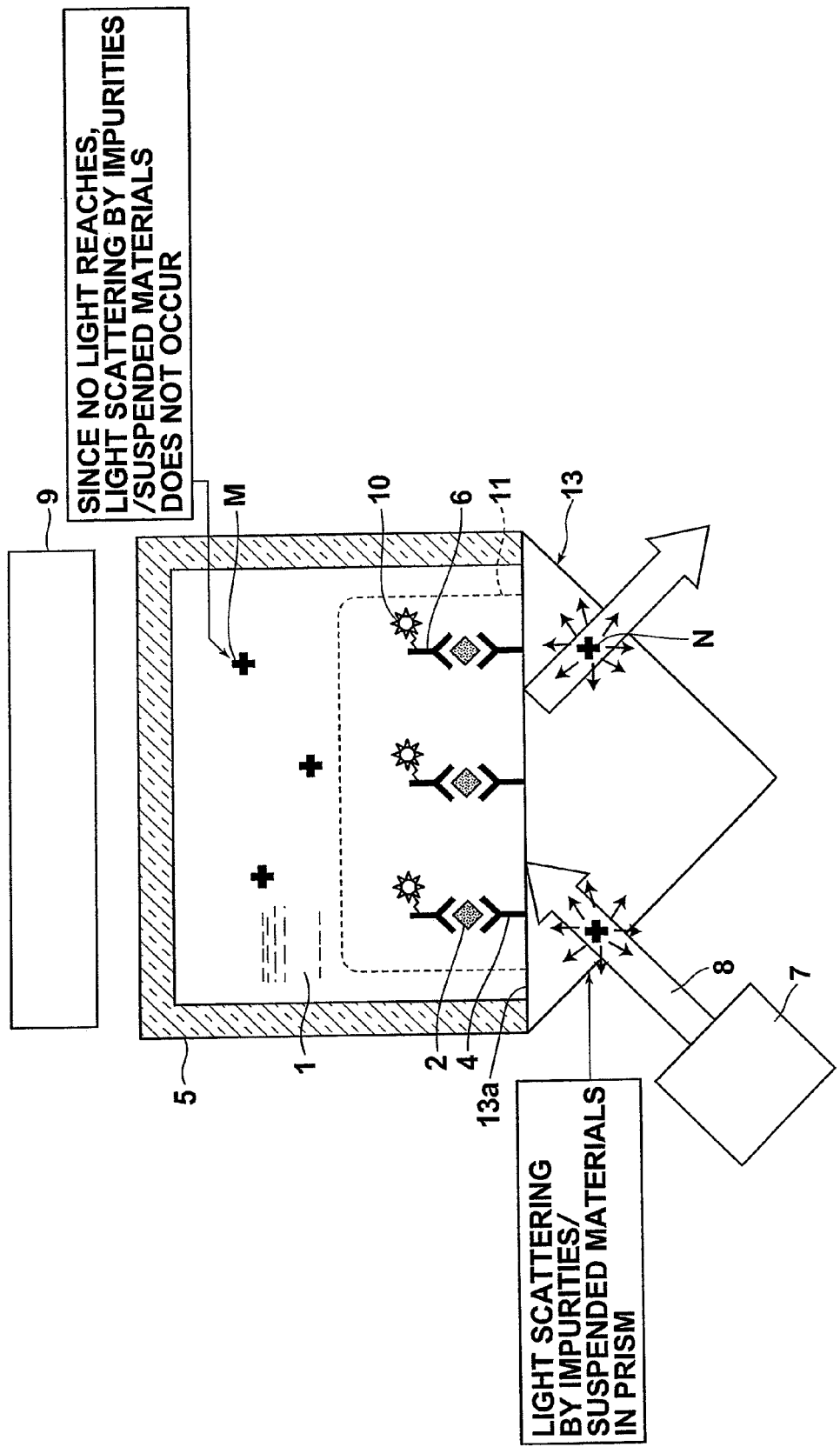

FLUORESCENCE ANALYSIS APPARATUS

BACKGROUND OF THE INVENTION

1. Field of the Invention

This invention relates to a fluorescence analysis apparatus for detecting a specific substance, which is contained in a sample, by use of a fluorometric analysis technique. This invention particularly relates to a fluorescence analysis apparatus of a type, in which a sensor section is dipped in a liquid sample.

2. Description of the Related Art

Heretofore, in fields of biological analyses, and the like, a fluorometric analysis technique has been used widely as an analysis technique, which has a high sensitivity and is easy to perform. The fluorometric analysis technique is the technique, wherein exciting light having a specific wavelength is irradiated to a sample expected to contain a substance to be analyzed, which substance is capable of producing fluorescence by being excited by the exciting light having the specific wavelength, wherein the fluorescence having thus been produced by the substance to be analyzed is detected, and wherein the presence of the substance to be analyzed is thereby confirmed. In cases where the substance to be analyzed is not a fluorescent substance, a technique has heretofore been conducted widely, wherein a specific binding substance, which has been labeled with a fluorescent substance and is capable of undergoing the specific binding with the substance to be analyzed, is brought into contact with the sample, wherein the fluorescence is detected in the same manner as that described above, and wherein the occurrence of the specific binding, i.e. the presence of the substance to be analyzed, is thereby confirmed.

FIG. 13 is a schematic side view showing an example of a conventional fluorescence analysis apparatus for carrying out a fluorometric analysis technique utilizing a labeled specific binding substance. By way of example, the fluorescence analysis apparatus illustrated in FIG. 13 is utilized for detecting an antigen 2, which is contained in a sample 1. The fluorescence analysis apparatus illustrated in FIG. 13 comprises a base plate 3, on which a primary antibody 4 capable of undergoing the specific binding with the antigen 2 has been coated. The fluorescence analysis apparatus also comprises a sample support section 5, which is formed on the base plate 3. The sample 1 is caused to flow within the sample support section 5. A secondary antibody 6, which has been labeled with a fluorescent substance 10 and is capable of undergoing the specific binding with the antigen 2, is then caused to flow within the sample support section 5. Thereafter, exciting light 8 is irradiated from a light source 7 toward a surface area of the base plate 3. Also, an operation for detecting the fluorescence is performed by a photodetector 9. In cases where the predetermined fluorescence is detected by the photodetector 9, the specific binding of the secondary antibody 6 and the antigen 2 with each other, i.e. the presence of the antigen 2 in the sample, is capable of being confirmed.

In the example described above, the substance whose presence is actually confirmed with the fluorescence detecting operation is the secondary antibody 6. If the secondary antibody 6 does not undergo the specific binding with the antigen 2, the secondary antibody 6 will be carried away and will not be present on the base plate 3. Therefore, in cases where the presence of the secondary antibody 6 on the base plate 3 is detected, the presence of the antigen 2, which is the substance to be analyzed, is capable of being confirmed indirectly.

Particularly, with the rapid advances made in enhancement of performance of photodetectors, such as the advances made in cooled CCD image sensors, in recent years, the fluorometric analysis technique described above has become the means essential for biological studies. The fluorometric analysis technique has also been used widely in fields other than the biological studies. In particular, with respect to the visible region, as in the cases of FITC (fluorescence wavelength: 525 nm, quantum yield: 0.6), Cy5 (fluorescence wavelength: 680 nm, quantum yield: 0.3), and the like, fluorescent dyes having high quantum yields exceeding 0.2, which serves as a criterion for use in practice, have been developed. It is thus expected that the fields of the application of the fluorometric analysis technique will become wide even further.

Also, a fluorometric analysis technique utilizing an evanescent wave has heretofore been proposed. FIG. 14 is a schematic side view showing an example of a conventional fluorescence analysis apparatus for carrying out a fluorometric analysis technique utilizing an evanescent wave. In FIG. 14, similar elements are numbered with the same reference numerals with respect to FIG. 13.

In the fluorescence analysis apparatus illustrated in FIG. 14, in lieu of the base plate 3 described above, a prism (a dielectric material block) 13 is utilized. A metal film 20 has been formed on a surface of the prism 13. Also, the exciting light 8 having been produced by the light source 7 is irradiated through the prism 13 under the conditions such that the exciting light 8 may be totally reflected from the interface between the prism 13 and the metal film 20. With the constitution of the fluorescence analysis apparatus illustrated in FIG. 14, at the time at which the exciting light 8 is totally reflected from the interface described above, an evanescent wave 11 oozes out to the region in the vicinity of the interface described above, and the secondary antibody 6 is excited by the evanescent wave 11. Also, the fluorescence detecting operation is performed by the photodetector 9 located on the side of the sample 1, which side is opposite to the side of the prism 13. (In the cases of FIG. 14, the photodetector 9 is located on the upper side.)

With the fluorescence analysis apparatus illustrated in FIG. 14, the exciting light 8 impinges upon the aforesaid interface from below in FIG. 14 and at an angle such that the exciting light 8 may be totally reflected from the aforesaid interface. As a result, the evanescent wave 11, which is capable of reaching only a region of several hundreds of nanometers from the aforesaid interface, arises and excites the secondary antibody 6. Therefore, it is possible to minimize the occurrence of the problems in that the exciting light, which has been reflected and scattered by the liquid sample 1, and the fluorescence (self-fluorescence), which has been produced from the liquid sample 1 and the vessel having been excited by the exciting light 8, impinge upon the photodetector 9 and constitute the background with respect to the fluorescence signal to be detected. Accordingly, the evanescent fluorometric analysis technique described above has attracted particular attention for serving as a technique, which is capable of markedly suppressing (light) noise than with the conventional fluorometric analysis techniques, and with which the substance to be analyzed is capable of being fluorometrically analyzed in units of one molecule.

The fluorescence analysis apparatus illustrated in FIG. 14 is the surface plasmon enhanced fluorescence analysis apparatus, which has the sensitivity having been enhanced markedly among the fluorescence analysis apparatuses utilizing the evanescent fluorometric analysis technique. With the surface plasmon enhanced fluorescence analysis apparatus, wherein the metal film 20 is formed, at the time at which the exciting light 8 is irradiated through the prism 13, the surface plasmon arises in the metal film 20, and the fluorescence is amplified by the electric field amplifying effect of the surface plasmon. A certain simulation has revealed that the fluorescence intensity in the cases described above is amplified by a factor of approximately 1,000. The surface plasmon enhanced fluorescence analysis apparatus of the type described above is described in, for example, Japanese Patent Application Publication No. 10 (1998)-078390.

Also, as described in, for example, U.S. Pat. No. 4,703,182, as one of the apparatuses for carrying out the fluorometric analysis technique as described above, there has been known a fluorescence analysis apparatus comprising: (i) a light source for producing exciting light, (ii) a sensor section, which may be constituted of a rod-shaped glass section, or the like, the sensor section propagating the exciting light through the interior of the sensor section, the sensor section radiating out the thus propagated exciting light from an outside surface of the sensor section, such that the exciting light having thus been radiated out may excite a fluorescent substance for indicating the presence of a substance to be analyzed in a liquid sample, and (iii) a photodetector for detecting the fluorescence, which has been produced by the fluorescent substance when the fluorescent substance is excited by the exciting light. In cases where the analysis is to be performed by use of the aforesaid type of the fluorescence analysis apparatus, ordinarily, the sensor section is dipped in the liquid sample, and the fluorescent substance is excited by the exciting light, which has been radiated out from the sensor section into the liquid sample. Also, the fluorescence, which has been produced by the fluorescent substance having thus been excited by the exciting light, is detected by the photodetector.

In, for example, U.S. Pat. No. 4,582,809 and Japanese Unexamined Patent Publication No. 2006-047250, it is indicated that an optical fiber may be employed as the sensor section described above. Particularly, in, for example, U.S. Pat. No. 4,582,809, it is described that a fluorescent substance may be excited by an evanescent wave, which oozes out from the surface of the optical fiber.

The fluorescence analysis apparatus utilizing the sensor section, which is dipped in the liquid sample in the manner described above, has the advantages over a fluorescence analysis apparatus of a type, in which the sensor section is built in a part of a liquid vessel, and in which the liquid sample is introduced into the liquid vessel by use of a pump, or the like, in that the constitution of the fluorescence analysis apparatus is capable of being kept simple, and in that the cost of the fluorescence analysis apparatus is capable of being kept low.

However, with the conventional fluorescence analysis apparatus utilizing the sensor section, which is dipped in the liquid sample, the problems are encountered in that, in cases where an analysis is to be made with respect to a substance to be analyzed, the quantity of which is markedly small on the order of, for example, 1 pmol (picomol)/l (liter), a sufficient analysis accuracy is not capable of being obtained. The aforesaid problems are encountered markedly in cases where a colored liquid, such as whole blood, blood serum, or urine, which contains comparatively large quantities of absorbing and scattering constituents other than the substance to be analyzed, is the liquid sample, and in cases where the sensor section is constituted of a rod-shaped material made from glass, an integrally molded transparent resin, or the like, the cost of which is low, in lieu of being constituted of an optical fiber provided with a cladding layer or a covering layer. The aforesaid problems are caused to occur by a phenomenon wherein, while the exciting light and/or the received light is being propagated in the rod-shaped glass, or the like, which acts as an optical waveguide, the exciting light and/or the received light is brought into contact with the liquid sample at an interface, is thus scattered or absorbed, and is thereby attenuated. In order for the adverse effects of the aforesaid problems to be suppressed, ordinarily, the optical fiber provided with the cladding layer or the covering layer is often utilized as the sensor section. However, in the aforesaid fields, in which various articles are desired to be disposable, in cases where the aforesaid optical fiber is utilized as the sensor section, the cost of the expendable supplies is not capable of being kept low. Therefore, the sensor section constituted of the optical fiber is not capable of being employed for reasons of cost.

Also, in cases where a washing process for removing unnecessary constituents is provided, the rod-shaped sensor section, the cost of which is low, is capable of being employed. However, in such cases, a liquid transfer mechanism, such as a dispenser and a pump, the cost of which is high, becomes necessary for the washing operation, and the cost of the fluorescence analysis apparatus is not capable of being kept low.

Further, with the sensor section for making the fluorescence analysis in the state in which the sensor section is dipped in a liquid, such as the liquid sample, there is the risk that a reflectivity of the exciting light and/or the received light at the aforesaid interface and the total reflection conditions of an optical path, or the like, will alter in accordance with the technique for inserting the sensor section into the liquid, the quantity of the liquid, sway of the liquid, and the like. Therefore, with the sensor section for making the fluorescence analysis in the state in which the sensor section is dipped in the liquid, it is not always possible to keep good analysis reproducibility.

SUMMARY OF THE INVENTION

The primary object of the present invention is to provide a fluorescence analysis apparatus, which is capable of being furnished at a low cost, and in which a sensor section capable of being utilized as expendable supplies at a cost as low as a disposable article is employed, such that an analysis is capable of being made with respect to a trace amount constituent, which is contained in a colored sample, such as whole blood, blood serum, or urine, or in a sample having light scattering characteristics, and such that good analysis reproducibility is capable of being kept.

The present invention provides a first fluorescence analysis apparatus of a type, in which a sensor section for propagating exciting light is dipped in a liquid sample, wherein problems are capable of being prevented from occurring in that exciting light and/or fluorescence is absorbed or scattered by the liquid sample, or the like, clinging to an outside surface of the sensor section. Specifically, the present invention provides a first fluorescence analysis apparatus, comprising:

i) a light source for producing exciting light, ii) a sensor section for propagating the exciting light through the interior of the sensor section to radiate out the thus propagated exciting light from an outside surface of the sensor section, such that the exciting light having thus been radiated out may excite a fluorescent substance for indicating the presence of a substance to be analyzed in a liquid sample, and iii) a photodetector for detecting the fluorescence, which has been produced by the fluorescent substance when the fluorescent substance is excited by the exciting light, wherein the improvement comprises the provision of:

a) sensor section actuating means for dipping the sensor section in the liquid sample, and thereafter moving the sensor section into a predetermined atmosphere, which is substantially free from occurrence of absorption or scattering of the exciting light and the fluorescence, and b) control means for actuating the light source and the photodetector in a state, in which the sensor section has been located in the predetermined atmosphere, and thereby causing a fluorescence detecting operation to be performed.

The first fluorescence analysis apparatus in accordance with the present invention should preferably be modified such that the sensor section propagates the exciting light in a guided mode, such that an evanescent wave may ooze out from the outside surface of the sensor section and may excite the fluorescent substance.

Also, the term "predetermined atmosphere" as used herein means the atmosphere, in which the extent of the scattering falls within the diameter range smaller than the diameter range capable of being regarded as "Mie scattering" (i.e., such that the diameter of the scattering body is equal to at most the wavelength), and in which the extent of the absorption falls within the range of at most 1%. Specifically, for example, the predetermined atmosphere may be air or a buffer liquid, which is under ordinary atmospheric conditions.

Further, the aforesaid predetermined atmosphere should preferably be an atmosphere, which does not contain the liquid sample and the fluorescent substance that acts as a label.

Furthermore, the first fluorescence analysis apparatus in accordance with the present invention should preferably be modified such that the sensor section actuating means is constituted of:

a rotating section, which is provided with at least a region for retaining the liquid sample, and a region for retaining the predetermined atmosphere, and which is capable of being rotated such that the region for retaining the liquid sample and the region for retaining the predetermined atmosphere may be successively kept stationary at a predetermined position, and reciprocal movement means for introducing the sensor section into the liquid sample at the time, at which the rotating section is kept stationary and at which the liquid sample has been located at the predetermined position, and for introducing the sensor section into the predetermined atmosphere at the time, at which the rotating section is kept stationary and at which the predetermined atmosphere has been located at the predetermined position.

Also, particularly, in cases where the substance to be analyzed is an antigen, the first fluorescence analysis apparatus in accordance with the present invention should preferably be modified such that the fluorescence analysis apparatus further comprises a reaction vessel for retaining a liquid containing an antibody, which has been labeled with the fluorescent substance and which is capable of undergoing binding with an antigen acting as the substance to be analyzed in the liquid sample, and the sensor section actuating means is constituted such that, after the sensor section actuating means has dipped the sensor section in the liquid sample, the sensor section actuating means dips the sensor section in the liquid retained in the reaction vessel and thereafter moves the sensor section into the predetermined atmosphere.

Further, the first fluorescence analysis apparatus in accordance with the present invention should preferably be modified such that a necessary reagent, the sensor section, the reaction vessel, and the like, are supplied and scrapped as a set.

The present invention also provides a second fluorescence analysis apparatus, comprising:

i) a light source for producing exciting light, ii) a sensor section for propagating the exciting light, which has entered into the sensor section from one end of the sensor section, through the interior of the sensor section to radiating out an evanescent wave from the other end of the sensor section, such that the exciting light may excite a fluorescent substance for indicating the presence of a substance to be analyzed in a liquid sample, in which the other end of the sensor section is dipped, and iii) a photodetector for detecting the fluorescence, which has been produced by the fluorescent substance when the fluorescent substance is excited by the exciting light, the sensor section being provided with:

a) an approximately cylindrical sensor section main body, and b) a tubular cover section for surrounding the sensor section main body, such that space may intervene between the cover section and an outside peripheral surface of the sensor section main body, which outside peripheral surface is adjacent at least to the other end of the sensor section, the cover section being provided with a blocking section for blocking the space, which intervenes between the cover section and the outside peripheral surface of the sensor section main body, at an end of the cover section, which end is located on the side of the other end of the sensor section.

The space described above may be an air layer. Alternatively, the space described above may be a vacuum.

The second fluorescence analysis apparatus in accordance with the present invention may be modified such that a rib for reinforcement is formed at a part of the sensor section main body, at which part the exciting light is not reflected, such that the rib may form a bridge between the part of the sensor section main body, at which part the exciting light is not reflected, and the cover section.

Also, the second fluorescence analysis apparatus in accordance with the present invention should preferably be modified such that the cover section is molded or coated with a material, which is capable of absorbing the exciting light and/or the fluorescence.

Further, the second fluorescence analysis apparatus in accordance with the present invention should preferably be modified such that the cover section is formed with integral molding processing together with the sensor section main body. Furthermore, the second fluorescence analysis apparatus in accordance with the present invention may be modified such that the cover section is provided with an engagement section for engaging with a support section of a support device, which supports the sensor section at a predetermined position.

Also, the second fluorescence analysis apparatus in accordance with the present invention should preferably be modified such that the sensor section main body propagates the exciting light in a guided mode.

Further, the second fluorescence analysis apparatus in accordance with the present invention should preferably be modified such that a ligand, which is capable of undergoing specific binding with the substance to be analyzed, is fixed to an outside surface of the other end of the sensor section.

Furthermore, the second fluorescence analysis apparatus in accordance with the present invention may be modified such that a necessary reagent, the sensor section, a reaction vessel, and the like, are supplied and scrapped as a set.

The inventors have found that the aforesaid problems encountered with the conventional fluorescence analysis apparatuses, i.e. the problems occurring in that a sufficient analysis accuracy is not capable of being obtained in cases where an analysis is to be made with respect to a trace amount of the substance to be analyzed by use of the sensor section, the cost of which is low, and with an apparatus, the cost of which is low, are caused to occur by a phenomenon such that, in cases where the liquid sample, or the like, is present around the sensor section, which is being dipped in the liquid sample, the exciting light and/or the fluorescence is absorbed or scattered by the liquid sample, and such that, as a result, little fluorescence is detected by the photodetector.

The present invention has been made on the basis of the findings described above. Specifically, with the first fluorescence analysis apparatus in accordance with the present invention, the sensor section is moved into the predetermined atmosphere, which is substantially free from the occurrence of the absorption or the scattering of the exciting light and the fluorescence, and the excitation of the fluorescent substance and the fluorescence detecting operation are performed in this state. Therefore, the adverse effects of the absorption and the scattering described above are capable of being eliminated, and the analysis with respect to a trace amount of the substance to be analyzed is capable of being made with a sufficient accuracy.

With the first fluorescence analysis apparatus in accordance with the present invention, wherein the sensor section actuating means is constituted of the rotating section and the reciprocal movement means described above, the analysis is capable of being made markedly efficiently.

With the second fluorescence analysis apparatus in accordance with the present invention, the sensor section is provided with: (a) the approximately cylindrical sensor section main body, and (b) the tubular cover section for surrounding the sensor section main body, such that the space may intervene between the cover section and the outside peripheral surface of the sensor section main body, which outside peripheral surface is adjacent at least to the other end of the sensor section. The other end of the sensor section is the end, from which the evanescent wave is radiated out. Also, the space, which intervenes between the cover section and the outside peripheral surface of the sensor section main body, is blocked at the end of the cover section, which end is located on the side of the other end of the sensor section. Therefore, with the second fluorescence analysis apparatus in accordance with the present invention, in cases where the sensor section is dipped in the liquid sample such that the liquid surface of the liquid sample may be located at a position lower than the top end of the cover section, the cover section comes into contact with the liquid sample. Also, in such cases, as for the sensor section main body, in which the exciting light and/or the received light is to be propagated, only the end face, i.e. the sensing part, of the sensor section main body on the side of the other end of the sensor section, from which the evanescent wave is to be radiated out, comes into directly contact with the liquid sample. Therefore, it is possible to prevent the problems from occurring in that the outside peripheral surface of the sensor section main body comes into direct contact with the liquid sample.

Therefore, with the second fluorescence analysis apparatus in accordance with the present invention, the adverse effects of the absorption and the scattering described above are capable of being eliminated, and the analysis with respect to a trace amount of the substance to be analyzed is capable of being made with a sufficient accuracy. Also, with the second fluorescence analysis apparatus in accordance with the present invention, wherein the outside peripheral surface of the sensor section main body is not brought into contact with the liquid, such as the liquid sample, there is no risk that, as in cases where the fluorescence analysis is made in the state in which the sensor section is dipped in the liquid, the total reflection conditions will alter in accordance with the technique for inserting the sensor section into the liquid, the quantity of the liquid, sway of the liquid, and the like. Therefore, it is possible to keep good analysis reproducibility. Also, since the space described above is capable of acting as a cladding layer, an optical fiber provided with a cladding layer, the cost of which optical fiber is high, need not be used for the sensor section. Therefore, the cost of the sensor section is capable of being kept low.

Further, with the second fluorescence analysis apparatus in accordance with the present invention, wherein the rib for reinforcement is formed at the part of the sensor section main body, at which part the exciting light is not reflected, such that the rib may form a bridge between the part of the sensor section main body, at which part the exciting light is not reflected, and the cover section, the intensity of the cover section is capable of being reinforced.

Furthermore, with the second fluorescence analysis apparatus in accordance with the present invention, wherein the cover section is molded or coated with the material, which is capable of absorbing the exciting light and/or the fluorescence, the cover section is capable of absorbing, for example, scattered light, which is caused to occur in cases where, for example, the exciting light and/or the fluorescence is scattered by impurities contained in the sensor section main body, and the like. Therefore, the problems are capable of being prevented from occurring in that the scattered light described above is detected by the photodetector.

Also, with the second fluorescence analysis apparatus in accordance with the present invention, wherein the cover section is formed with the integral molding processing together with the sensor section main body, the sensor section is capable of being formed at a low cost. Therefore, the sensor section having thus been formed is appropriate for use in diagnostic systems, in which the sensor section is desired to be disposable.

Further, with the second fluorescence analysis apparatus in accordance with the present invention, wherein the cover section is provided with the engagement section for engaging with the support section of the support device, which supports the sensor section at the predetermined position, the sensor section is capable of being located easily at the predetermined position, such that the total reflection conditions may not alter.

BRIEF DESCRIPTION OF THE DRAWINGS

FIG. 7A is a sectional front view showing a sensor section in the fluorescence analysis apparatus of FIG. 6, FIG. 7B is a side view showing the sensor section in the fluorescence analysis apparatus of FIG. 6, FIG. 8 is a schematic side view showing a third embodiment of the fluorescence analysis apparatus in accordance with the present invention, FIG. 13 is a schematic side view showing an example of a conventional fluorescence analysis apparatus for carrying out a fluorometric analysis technique utilizing a labeled specific binding substance, and FIG. 14 is a schematic side view showing an example of a conventional fluorescence analysis apparatus for carrying out a fluorometric analysis technique utilizing an evanescent wave.

DESCRIPTION OF THE PREFERRED EMBODIMENTS

The present invention will hereinbelow be described in further detail with reference to the accompanying drawings.

A fluorescence analysis apparatus 100-1, which is a first embodiment of the fluorescence analysis apparatus in accordance with the present invention, will be described hereinbelow with reference to FIG. 1, FIG. 2, and FIGS. 3A to 3K.

Figure 1:
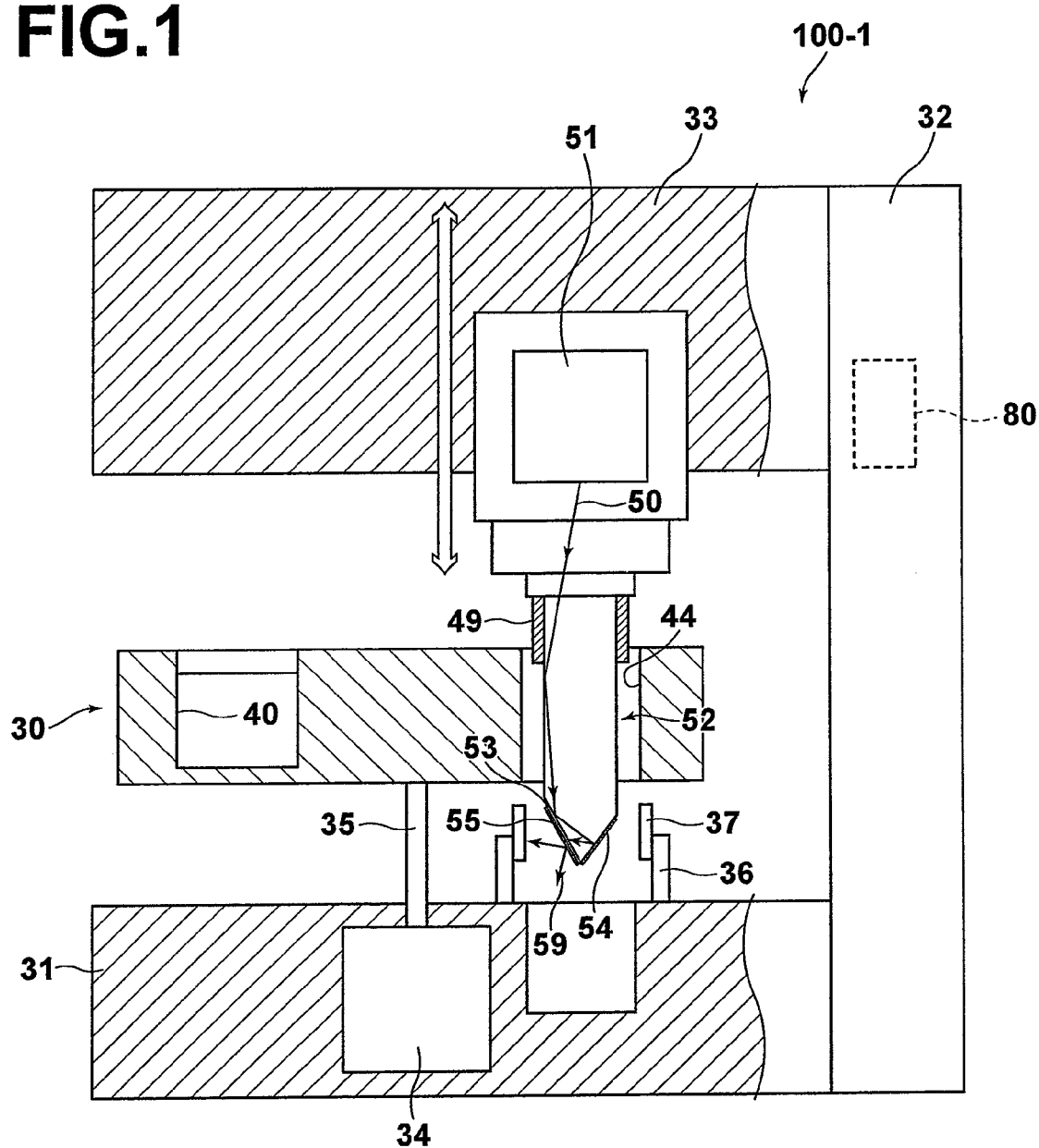
FIG. 1 is a schematic side view showing a first embodiment of the fluorescence analysis apparatus in accordance with the present invention.
Figure 2:
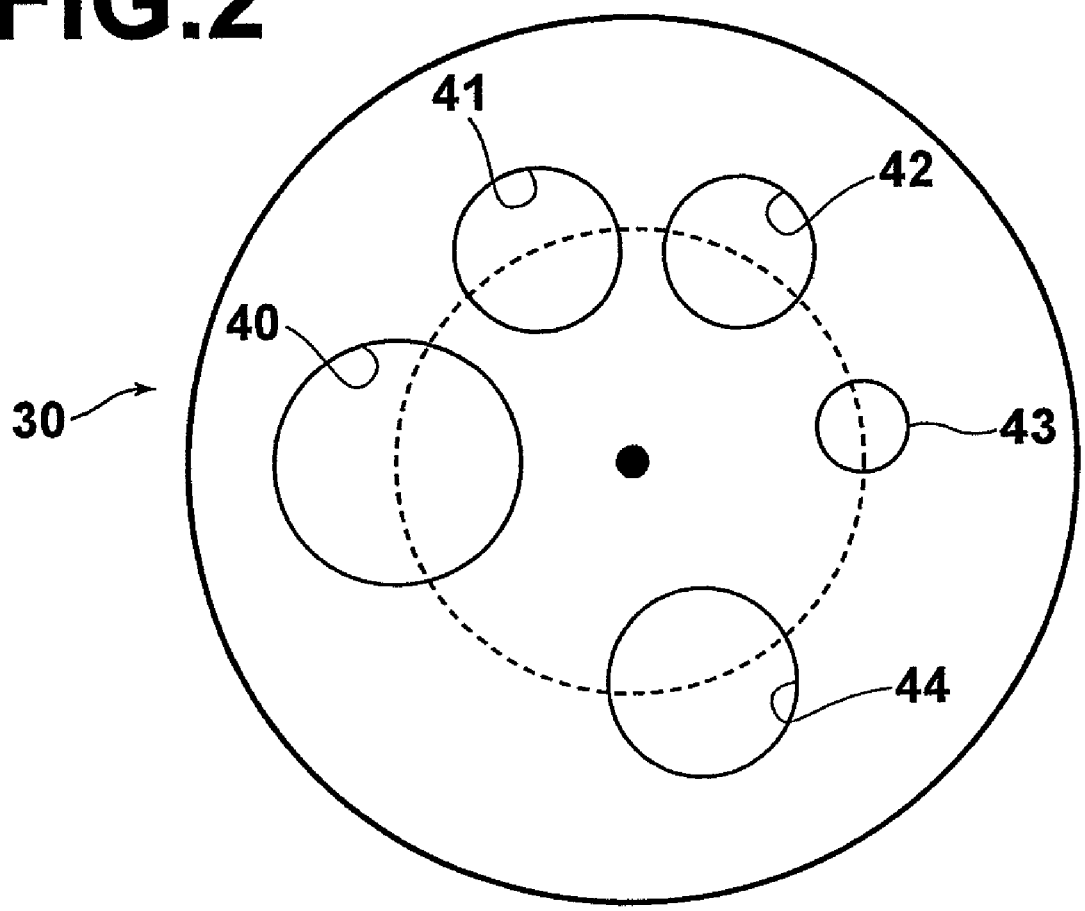
FIG. 2 is a plan view showing a part of the fluorescence analysis apparatus of FIG. 1, FIGS. 3A to 3K are schematic views successively showing analysis steps performed by the fluorescence analysis apparatus of FIG. 1.

FIG. 1 is a schematic side view showing the fluorescence analysis apparatus 100-1. FIG. 2 is a plan view showing a turret 30 utilized in the fluorescence analysis apparatus 100-1 of FIG. 1. As illustrated in FIG. 1, the fluorescence analysis apparatus 100-1 comprises the turret 30. The fluorescence analysis apparatus 100-1 also comprises a support base 31 for supporting the turret 30 in a horizontal state such that the turret 30 is capable of being moved. The fluorescence analysis apparatus 100-1 further comprises a vertical member 32, which extends vertically from the support base 31. The fluorescence analysis apparatus 100-1 still further comprises a vertical moving base 33, which is supported by the vertical member 32 such that the vertical moving base 33 is capable of being moved in the vertical directions by driving means (not shown).

A stepping motor 34 is secured to the support base 31, and the turret 30 is secured to a drive shaft 35 of the stepping motor 34. Therefore, when the stepping motor 34 is actuated, the turret 30 is rotated around the drive shaft 35 of the stepping motor, i.e. in the horizontal plane. Also, a fixture 36 is fitted to the top surface of the support base 31, and a photodetector 37, which may be constituted of, for example, a photodiode, is fitted to the fixture 36. By way of example, the photodetector 37 may be constituted of a pair of photodetectors, which are located so as to stand facing each other at a spacing from each other.

As illustrated in FIG. 2, at the top surface of the turret 30, a liquid sample vessel 40, a reaction vessel 41, a buffer liquid vessel 42, and a sensor section support hole 43 are formed as hole regions having predetermined depths. Also, a through-hole 44 is formed in the turret 30. The liquid sample vessel 40, the reaction vessel 41, the buffer liquid vessel 42, the sensor section support hole 43, and the through-hole 44 are located at predetermined angle intervals from one another such that the center points of the liquid sample vessel 40, the reaction vessel 41, the buffer liquid vessel 42, the sensor section support hole 43, and the through-hole 44 are located on a single common circle around the rotation axis of the turret 30.

The vertical moving base 33 is provided with a light source 51, which may be constituted of a semiconductor laser, or the like, for producing exciting light 50 having a wavelength of, for example, 635 nm. The vertical moving base 33 is also provided with a chuck 49 for releasably supporting the sensor section 52. The sensor section 52 is formed into a rod-shaped section by use of a transparent resin, an optical glass, or the like. As illustrated in FIG. 1, the bottom end of the sensor section 52 is shaped such that two end faces may intersect at an acute angle with each other. Also, a metal film 53 is formed on one of the two end faces of the bottom end of the sensor section 52, and a reflecting film 54 acting as a mirror surface is formed on the other end face of the bottom end of the sensor section 52. Further, an inflexible film 55 is formed on the metal film 53. The metal film 53 is constituted of, for example, a gold film having been formed with sputtering processing. The film thickness of the metal film 53 is set at 50 nm. Furthermore, the inflexible film 55 is formed with processing, wherein a film of a polystyrene type polymer having a refractive index of 1.59 is formed with a spin coating technique on the metal film 53. The film thickness of the inflexible film 55 is set at 20 nm.

The stepping motor 34, the vertical moving base 33, the light source 51, and the photodetector 37 are connected to a control circuit 80, which is located within the vertical member 32. The control circuit 80 appropriately controls the operation timing of each of the stepping motor 34, the vertical moving base 33, the light source 51, and the photodetector 37. For example, the actuation of the stepping motor 34, i.e. the rotating operation of the turret 30, is controlled by the control circuit 80 in the manner synchronized with the actuation of the vertical moving base 33, the light source 51, and the photodetector 37.

As an example of a particularly preferable resin for constituting the sensor section 52, there may be mentioned ZEONEX (trade name) 330R (refractive index: 1.50), supplied by Nippon Zeon Co., Ltd. Besides the material described above, the sensor section 52 may be formed by use of a known resin, a known optical glass, or the like. From the view point of the cost, the resin is more preferable than the optical glass. In cases where the sensor section 52 is made from a resin, the resin may be selected from a polymethyl methacrylate (PMMA), a polycarbonate (PC), an amorphous polyolefin (APO) containing a cycloolefin, and the like.

By way of example, the chuck 49 described above may be provided with a mechanical holding mechanism, which will be described later. The chuck 49 has a circular cylinder-shaped end. The interior of the chuck 49 is communicated with air jetting-out means (not shown), such as a blower. The chuck 49 thus has the functions for supporting the sensor section 52 with the holding mechanism described above and jetting out air for stirring the liquid sample, or the like. The functions will be described later in detail.

By way of example, the object of the analysis with the embodiment of the fluorescence analysis apparatus 100-1 is a CRP antigen (molecular weight: 110,000 Da). A primary antibody (a monoclonal antibody), which is capable of undergoing the specific binding with the CRP antigen, has been fixed on the inflexible film 55. The primary antibody has been fixed to the inflexible film 55, which is constituted of a polymer, via, for example, PEG having a terminal introduced with a carboxyl group, by use of an amine coupling technique. Also, as a secondary antibody, a monoclonal antibody, which has been labeled with a fluorescent substance (Cy5, supplied by Ge-healthcare Co.), is employed. (The monoclonal antibody employed as the secondary antibody varies in epitope (antigenic determinant) from the primary antibody.)

By way of example, the aforesaid amine coupling technique comprises the steps (1), (2), and (3) described below. The example described below is of the cases wherein a 30 µl (microliter) cuvette/cell is used.

(1) Activation of a —COOH Group at a Linker End (Terminal)

A solution, which has been prepared by mixing 0.1M (mol) NHS and 0.4M EDC together in an equal volume ratio, is added in an amount of 30 µl, and the resulting mixture is allowed to stand for 30 minutes at the room temperature.

NHS: N-Hydrooxysuccinimide

EDC: 1-Ethyl-3-(3-dimethylaminopropyl) carbodiimide (2) Fixation of the Primary Antibody After washing with a PBS buffer (pH7.4) is performed five times, a primary antibody solution (500 µg/ml) is added in an amount of 30 µl, and the resulting mixture is allowed to stand for 30 to 60 minutes at the room temperature.

(3) Blocking of an Unreacted —COOH Group

After washing with the PBS buffer (pH7.4) is performed five times, 1M ethanolamine (pH8.5) is added in an amount of 30 µl, and the resulting mixture is allowed to stand for 20 minutes at the room temperature. Washing with the PBS buffer (pH7.4) is then performed five times.

The light source 51 is not limited to the semiconductor laser described above and may be selected from the other various kinds of the known light sources, such as LED's. Also, the photodetector 37 is not limited to the photodetector described above and may be selected from the other various kinds of the known devices, such as a CCD, a photomultiplier, and c-MOS. Further, in cases where the excitation wavelength is altered, a dye other than Cy5 is capable of being employed as a label.

How the fluorescence analysis apparatus 100-1 operates will be described hereinbelow with reference to FIGS. 3A to 3K, which successively show analysis steps performed by the fluorescence analysis apparatus of FIG. 1. In each of FIGS. 3A to 3K, for simplicity, the reference numerals are given to only the elements necessary for the explanation among the elements illustrated in FIG. 1.

Figure 3:
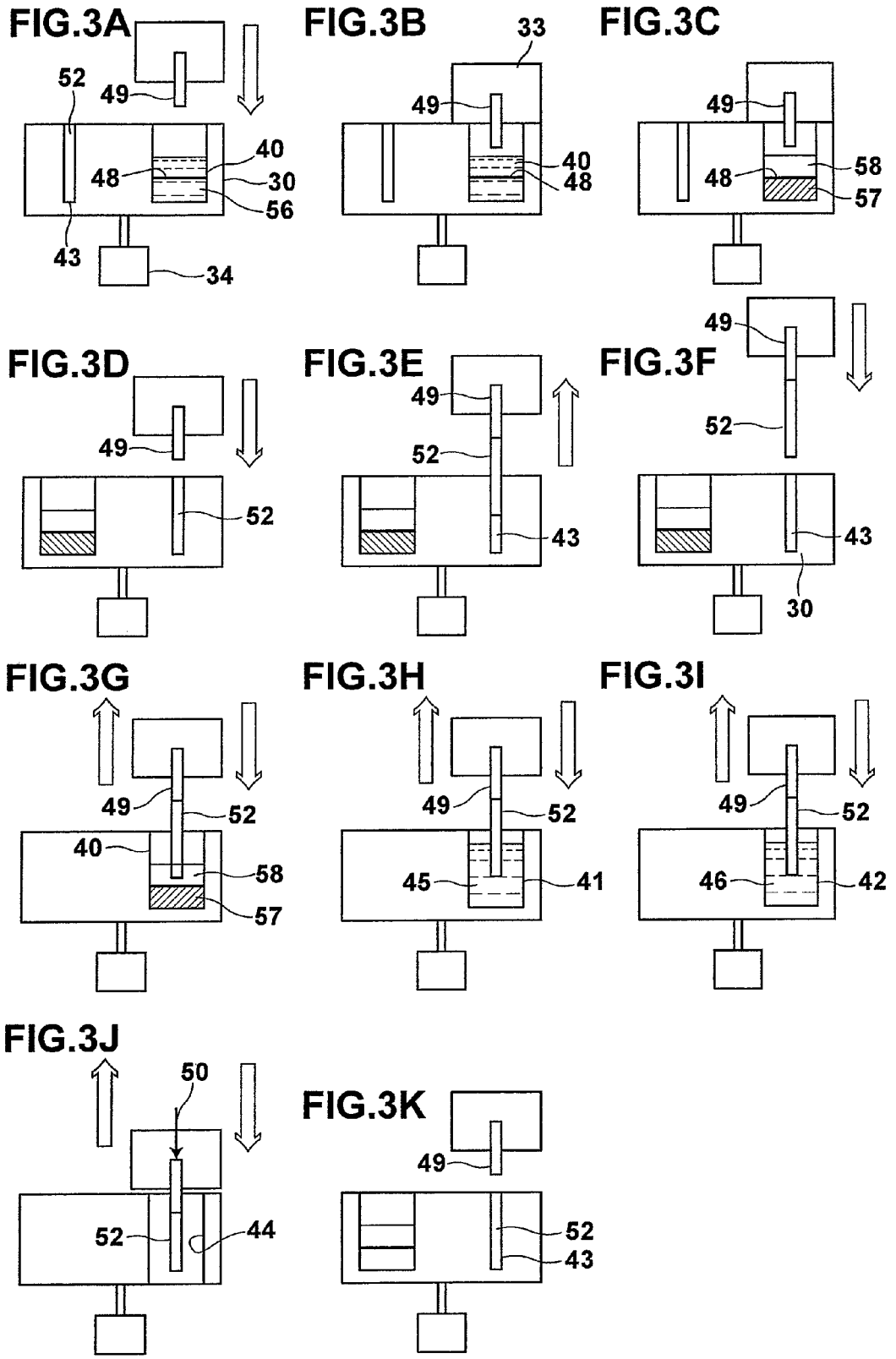

Firstly, in cases where the analysis is to be made, the sensor section 52 is previously accommodated in the sensor section support hole 43. Also, as illustrated in FIG. 3A, a predetermined quantity of whole blood 56 acting as the liquid sample is injected into the liquid sample vessel 40, and the turret 30 is rotated by a predetermined angle such that the liquid sample vessel 40 may be set at the position just under the chuck 49. Thereafter, as illustrated in FIG. 3B, the chuck 49 is moved down (i.e., the vertical moving base 33 is moved down), and the whole blood 56 is subjected to filtration through a filter 48, which is located in the liquid sample vessel 40, by an air pressure arising between the chuck 49 and the liquid sample vessel 40. As illustrated in FIG. 3C, with the filtration, the whole blood 56 is separated into blood corpuscles 57, which are comparatively heavy, and blood plasma 58.

In this state, the chuck 49 is pulled up, and the turret 30 is further rotated by a predetermined angle. As illustrated in FIG. 3D, the sensor section 52 having been accommodated in the sensor section support hole 43 is thus set at the position just under the chuck 49. In this state, the chuck 49 is moved down, and the sensor section 52 is supported by the chuck 49 in the manner such that a drill is held by an ordinary drilling machine. Also, as illustrated in FIG. 3E, the chuck 49 is pulled up, and the sensor section 52 is pulled out upwardly from the sensor section support hole 43.

As illustrated in FIG. 3F, the sensor section 52 is completely separated from the turret 30. Thereafter, as illustrated in FIG. 3G, the liquid sample vessel 40 is again set at the position just under the chuck 49. Also, in this state, the chuck 49 is moved down by a predetermined distance and is then moved up and down. As a result, the sensor section 52 having been supported by the chuck 49 is slightly moved up and down in the state in which the sensor section 52 is being dipped in the blood plasma 58. Therefore, in such cases, if the CRP antigen is contained in the blood plasma 58, the binding of the CRP antigen and the primary antibody, which has been fixed to the inflexible film 55 of the sensor section 52, with each other will be promoted.

Thereafter, the sensor section 52 is pulled up from the liquid sample vessel 40, and the turret 30 is then rotated by a predetermined angle. In this manner, as illustrated in FIG. 3H, the reaction vessel 41 is set at the position just under the chuck 49. The reaction vessel 40 accommodates a reaction liquid 45, which contains the secondary antibody having been labeled with the fluorescent substance as described above. Thereafter, the chuck 49 is moved down by a predetermined distance and is then moved up and down. As a result, the sensor section 52 having been supported by the chuck 49 is slightly moved up and down in the state in which the sensor section 52 is being dipped in the reaction liquid 45. Therefore, in such cases, if the CRP antigen has been bound with the primary antibody on the inflexible film 55 of the sensor section 52, the binding of the CRP antigen and the secondary antibody, which is contained in the reaction liquid 45, with each other will be promoted.

Thereafter, the sensor section 52 is pulled up from the reaction vessel 41, and the turret 30 is then rotated by a predetermined angle. In this manner, as illustrated in FIG. 3I, the buffer liquid vessel 42 is set at the position just under the chuck 49. Thereafter, the chuck 49 is moved down by a predetermined distance and is then moved up and down. As a result, the sensor section 52 is washed with a buffer liquid 46, which is accommodated in the buffer liquid vessel 42. Specifically, in cases where the aforesaid CRP antigen and the secondary antibody having been labeled with the fluorescent substance have been bound with each other, unnecessary matter other than the CRP antigen and the secondary antibody having been labeled with the fluorescent substance is washed off.

Thereafter, the sensor section 52 is pulled up from the buffer liquid vessel 42, and the turret 30 is then rotated by a predetermined angle. In this manner, as illustrated in FIG. 3J, the through-hole 44 is set at the position just under the chuck 49. Thereafter, the chuck 49 is moved down, and the sensor section 52 is thus located within the through-hole 44. In this state, air alone is present around the sensor section 52. Therefore, the sensor section 52 is thus located in an atmosphere, which is substantially free from the occurrence of the absorption or the scattering of the exciting light and the fluorescence at the time of the fluorescence analysis described below.

The fluorescence analysis, which is performed in this state, will hereinbelow be described in detail with reference to FIG.

1, which illustrates the state described above. At the time of the fluorescence analysis, the light source 51 is actuated, and the exciting light 50, such as the laser beam, is produced by the light source 51. The majority of the exciting light 50 travels downwardly in a guided mode within the rod-shaped sensor section 52, while the total reflection is being iterated at the interface between the peripheral surface of the rod-shaped sensor section 52 and air. A part of the exciting light 50, which has thus been propagated within the sensor section 52, reaches the end face provided with the metal film 53, which end face is one of the two end faces having been formed obliquely at the bottom part of the sensor section 52. Also, a part of the exciting light 50, which has thus been propagated within the sensor section 52, is reflected from the reflecting film 54 and then reaches the end face provided with the metal film 53. The exciting light 50 is thus totally reflected from the end face provided with the metal film 53.

At this time, the evanescent wave oozes out from the interface between the end face of the sensor section 52 and the metal film 53. Therefore, in cases where the CRP antigen has been bound with the primary antibody on the inflexible film 55, the secondary antibody contained in the reaction liquid 45 is bound with the CRP antigen, and the fluorescent substance acting as the label of the secondary antibody is excited by the evanescent wave described above. The fluorescent substance having thus been excited by the evanescent wave produces fluorescence 59 having a predetermined wavelength, and the thus produced fluorescence 59 is detected by the photodetector 37. In cases where the photodetector 37 detects the fluorescence 59 having the predetermined wavelength, it is possible to confirm that the secondary antibody has been bound with the CRP antigen, i.e. that the CRP antigen is contained in the blood plasma 58 acting as the liquid sample. Also, in accordance with the intensity of a signal obtained from the detection of the fluorescence described above, it is possible to detect the concentration of the substance to be analyzed.

When the fluorescence analysis has been finished in the manner described above, the sensor section 52 is pulled up from the through-hole 44, and the turret 30 is then rotated by a predetermined angle. In this manner, as illustrated in FIG. 3K, the sensor section support hole 43 is set at the position just under the chuck 49. Thereafter, the chuck 49 is moved down, and the sensor section 52 is thus inserted into the sensor section support hole 43. The chuck 49 is then opened and moved up, and the sensor section 52 is thus released from the chuck 49. In this manner, the sensor section 52 is returned into the sensor section support hole 43. Thereafter, the turret 30 having thus been used is scrapped, and a new turret 30 is set in the fluorescence analysis apparatus 100-1. Therefore, the fluorescence analysis is capable of being performed without contamination being taken into consideration.

In this embodiment, as clear from the foregoing explanation, the sensor section actuating means is constituted of the turret 30, which acts as the rotating section, and the reciprocal movement means, which is provided with the vertical moving base 33 and the chuck 49. In cases where the turret 30 described above is used, the fluorescence analysis is capable of being performed markedly efficiently. However, the sensor section actuating means is not limited to the means described above and may be constituted of one of various other known mechanisms.

Also, in cases where contamination need not much be taken into consideration, the sensor section, or the like, may be washed, and a reagent may be loaded again. In this manner, it is possible to reuse the turret 30.

As described above, at the time at which the aforesaid fluorescence analysis is performed, the sensor section 52 is located in the atmosphere, which is substantially free from the occurrence of the absorption or the scattering of the exciting light 50 and the fluorescence 59. Therefore, the problems are capable of being prevented from occurring in that the intensity of the fluorescence 59 detected becomes low due to the absorption or the scattering of the fluorescence 59, and in that the accuracy of the analysis of the substance to be analyzed is affected adversely. Also, the problems are capable of being prevented from occurring in that the exciting light 50, such as the light having partially leaked out from the sensor section 52, is scattered and impinges upon the photodetector 37, and in that the analysis accuracy is thereby affected adversely.

Further, with this embodiment of the fluorescence analysis apparatus 100-1, the metal film 53 is formed on the end face of the sensor section 52, from which end face the evanescent wave oozes out. Therefore, the surface plasmon is excited at the metal film 53. Accordingly, the intensity of the exciting light 50 is enhanced by the electric field amplifying effect of the surface plasmon, and the fluorescence detection signal is capable of being obtained with a high signal-to-noise ratio.

Further, with this embodiment of the fluorescence analysis apparatus 100-1, wherein the inflexible film 55 having a film thickness of 20 nm is formed on the metal film 53, the problems are capable of being prevented from occurring in that the fluorescent substance acting as the label becomes close to the metal film 53 to an extent such that the metal quenching may occur. Therefore, with this embodiment of the fluorescence analysis apparatus 100-1, the metal quenching described above is not caused to occur. Accordingly, the electric field amplifying effect with the surface plasmon is capable of being obtained reliably, and the fluorescence is capable of being detected with a markedly high sensitivity.

Furthermore, with this embodiment of the fluorescence analysis apparatus 100-1, wherein the inflexible film 55 is made from the polystyrene type polymer, which is the hydrophobic material, the problems do not occur in that the molecules, which will cause the quenching to occur, such as metal ions and dissolved oxygen present in the liquid sample, enter into the interior of the inflexible film 55. Therefore, the problems are capable of being prevented from occurring in that the molecules described above deprive the exciting light 50 of the excitation energy. Accordingly, with this embodiment of the fluorescence analysis apparatus 100-1, a markedly high level of excitation energy is capable of being obtained, and the fluorescence is capable of being detected with a markedly high sensitivity.

With this embodiment of the fluorescence analysis apparatus 100-1, the secondary antibody is detected from the fluorescence analysis, and the substance to be analyzed, which is contained in the liquid sample, is thus detected indirectly. However, the fluorescence analysis apparatus in accordance with the present invention is also capable of being constituted for directly detecting the substance to be analyzed, which is the fluorescent substance.

Figure 4:
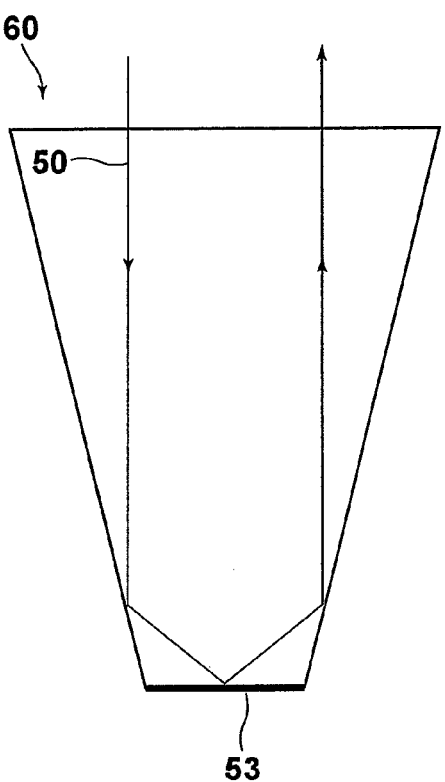
FIG. 4 is a schematic side view showing a different example of a sensor section.
Figure 5:
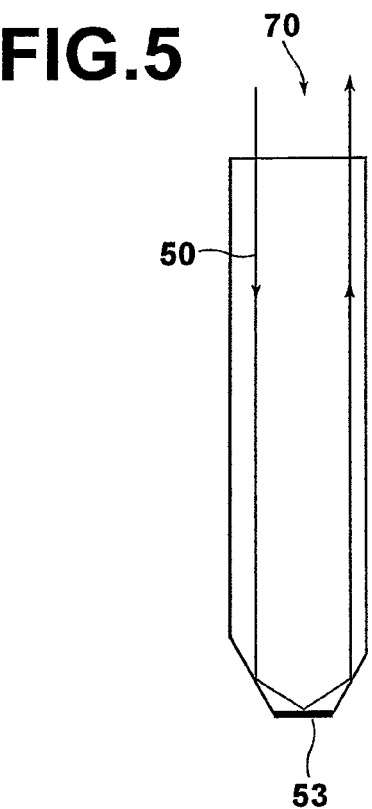
FIG. 5 is a schematic side view showing a further different example of a sensor section.

Also, the sensor section constituting the fluorescence analysis apparatus in accordance with the present invention is not limited to the sensor section 52 described above and may be constituted as, for example, a sensor section 60 having a shape as illustrated in FIG. 4 or a sensor section 70 having a shape as illustrated in FIG. 5. Further, the sensor section for propagating the exciting light in the guided mode is not limited to the rod-shaped sensor section described above and may be constituted of an optical fiber.

Furthermore, the embodiment of the fluorescence analysis apparatus 100-1 described above is constituted as the surface plasmon enhanced fluorescence analysis apparatus. However, the fluorescence analysis apparatus in accordance with the present invention is also capable of being constituted as a fluorescence analysis apparatus of the type in which the surface plasmon enhancement is not performed particularly (i.e., the fluorescence analysis apparatus of the type in which the metal film 53 in the embodiment described above is not formed).

Also, in the embodiment described above, air is employed as the atmosphere, which is substantially free from the occurrence of the absorption or the scattering of the exciting light and the fluorescence, and the excitation of the fluorescent substance and the fluorescence detecting operation are performed in air. Besides air, for example, a liquid, such as deionized water or PBS buffer, is also appropriated as the atmosphere described above. The fluorescence analysis apparatus in accordance with the present invention may also be constituted such that the excitation of the fluorescent substance and the fluorescence detecting operation are performed in the liquid described above.

Figure 6:
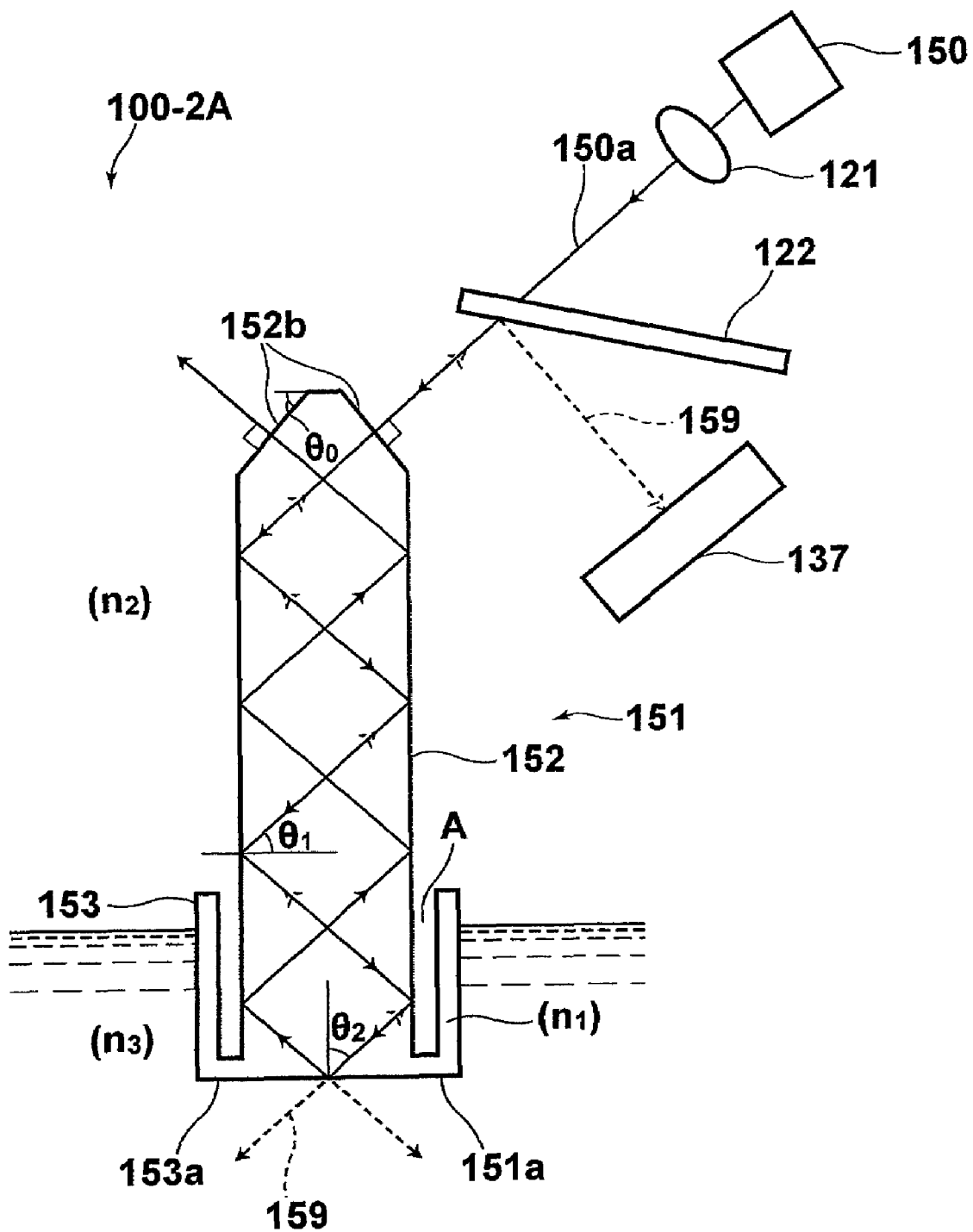
FIG. 6 is a conceptual view showing an approximate constitution of a second embodiment of the fluorescence analysis apparatus in accordance with the present invention.

A fluorescence analysis apparatus 100-2A, which is a second embodiment of the fluorescence analysis apparatus in accordance with the present invention, will be described hereinbelow with reference to FIG. 6 and FIGS. 7A and 7B. FIG. 6 is a conceptual view showing an approximate constitution of the fluorescence analysis apparatus 100-2A. FIG. 7A is a sectional front view showing a sensor section 151 in the fluorescence analysis apparatus 100-2A of FIG. 6. FIG. 7B is a side view showing the sensor section 151 in the fluorescence analysis apparatus 100-2A of FIG. 6. In FIG. 6 and FIGS. 7A and 7B, as an aid in facilitating the explanation, the side on which a light source 150 is located, i.e. the top side in the plane of the sheet of each of FIG. 6 and FIGS. 7A and 7B, is taken as the upper side.

As illustrated in FIG. 6, this embodiment of the fluorescence analysis apparatus 100-2A comprises a light source 150, which may be constituted of a semiconductor laser, or the like, for producing exciting light 150a having a wavelength of, for example, 635 nm. The fluorescence analysis apparatus 100-2A also comprises an optical system 121, which may be constituted of a collimator lens, or the like, for performing a beam regulation for the exciting light 150a having been produced by the light source 150. The fluorescence analysis apparatus 100-2A further comprises a sensor section 151 provided with an optical waveguide for propagating the exciting light 150a and fluorescence 159, which will be described later, in the interior of the sensor section 151. The fluorescence analysis apparatus 100-2A still further comprises a dichroic mirror 122 for transmitting light, which has a wavelength shorter than, for example, 645 nm, and reflecting light, which has a wavelength longer than, for example 645 nm, at a right angle. The fluorescence analysis apparatus 100-2A also comprises a photodetector 137, which may be constituted of a photodiode, or the like, for detecting the light having been reflected from the dichroic mirror 122.

By way of example, the sensor section 151 may be formed from a transparent resin having a refractive index of n1=1.7. Specifically, the sensor section 151 may be formed from a phenol resin (a phenol-formaldehyde resin) ("Test Method and Evaluation Results of Dynamic Characteristics of Plastic Materials <19>", T. Yasuda, Plastic, Vol. 52, No. 8, pp. 98-101). More specifically, the sensor section 151 may be formed by use of, for example, Tesralid (trade name) or Eyrie (trade name), supplied by Hoya Corp.

As illustrated in FIGS. 7A and 7B, this embodiment of the fluorescence analysis apparatus 100-2A has the feature in that the sensor section 151 is provided with: (a) an approximately cylindrical sensor section main body 152, and (b) a tubular cover section 153 for surrounding the sensor section main body 152, such that space A may intervene between the cover section 153 and an outside peripheral surface 152c of the sensor section main body 152, which outside peripheral surface is adjacent at least to the bottom end of the sensor section 151. The cover section 153 is provided with a blocking section 153a for blocking the space A, which intervenes between the cover section 153 and the outside peripheral surface 152c of the sensor section main body 152, at an end of the cover section 153, which end is located on the side of the bottom end of the sensor section 151. In this embodiment, the space A is taken as the air layer A and will hereinbelow be explained as the air layer A.

The sensor section main body 152 is formed from the material described above into an approximately circular cylinder-like shape having a diameter W of, for example, approximately 10 mm. As illustrated in FIG. 7A, on the top end side of the sensor section main body 152, slant faces 152b, 152b are formed on the right and left opposite sides, as viewed from the front. Each of the slant faces 152b, 152b makes an angle θ0 of, for example, approximately 53 degrees with respect to a top end face 152a of the sensor section main body 152, as viewed from the front. Also, the sensor section main body 152 and the cover section 153 are formed with integral molding processing such that the bottom end faces of the sensor section main body 152 and the cover section 153 may be approximately flat, i.e. such that a bottom end face 151a of the sensor section 151 may be approximately flat. In cases where the cover section 153 is formed with the integral molding processing together with the sensor section main body 152, the sensor section 151 is capable of being formed at a low cost. Therefore, the sensor section 151 having thus been formed is appropriate for use in diagnostic systems, in which the sensor section 151 is desired to be disposable.

Also, as described above, the sensor section 151 has a refractive index of n1=1.7. Therefore, in cases where the atmosphere around the sensor section 151 is, for example, air having a refractive index of n2=1, a critical angle θ is equal to 36.03 degrees. In cases where the atmosphere around the sensor section 151 is, for example, a physiological saline having a refractive index of n3=1.335, the critical angle θ is equal to 51.75 degrees. As illustrated in FIG. 6, in cases where the bottom end of the sensor section 151 is dipped in the physiological saline, such that the liquid surface of the physiological saline may be located at a height lower than the top end face of the cover section 153, the exciting light 150a may be irradiated so as to impinge upon the slant face 152b at a right angle. In such cases, the angle θ1, which is made between the horizontal plane and the light beam of the exciting light 150a at the peripheral surface of the sensor section main body 152, may be represented by θ1=37 degrees, and the angle θ2, which is made between the normal plane and the light beam of the exciting light 150a at the bottom end face 151a of the sensor section 151, may be represented by θ2=53 degrees. At the peripheral surface of the sensor section main body 152, around which air is present, the angle of θ1=37 degrees is larger than the critical angle of θ=36.03 degrees. Also, at the bottom end face 151a of the sensor section 151, around which the physiological saline is present, the angle of θ2=53 degrees is larger than the critical angle of θ=51.75 degrees. Therefore, the exciting light 150a is totally reflected within the sensor section main body 152 and at the bottom end face 151a of the sensor section 151.

At this time, for example, it may be desired that the exciting light 150a excites the fluorescent substance, which will be described later, at the bottom end face 151a of the sensor section 151 after being totally reflected four times within the sensor section main body 152. In such cases, as illustrated in FIG. 7A, a height H2 from the bottom end face 151a to the bottom end of the slant face 152b may be set at H2=4×W×tan θ1=30.14 mm. The values of the angle θ0, the diameter W, and the height H2 with respect to the sensor section main body 152 may be altered appropriately in accordance with the refractive indexes of air, the liquid, in which the sensor section 151 is to be dipped, and the like, such that the exciting light and/or the fluorescence may be totally reflected at the outside peripheral surface of the sensor section main body 152 and at the bottom end face 151a of the sensor section 151 at the time of the fluorescence analysis.

By way of example, the object of the analysis with the embodiment of the fluorescence analysis apparatus 100-2A is the CRP antigen (molecular weight: 110,000 Da). The primary antibody (a monoclonal antibody), which is capable of undergoing the specific binding with the CRP antigen, has been fixed on the bottom end face 151a. The primary antibody has been fixed to the bottom end face 151a via, for example, PEG having a terminal introduced with a carboxyl group, by use of the amine coupling technique. Also, as the secondary antibody, the monoclonal antibody, which has been labeled with the fluorescent substance (Cy5, supplied by Ge-healthcare Co.), is employed. (The monoclonal antibody employed as the secondary antibody varies in epitope (antigenic determinant) from the primary antibody.)

The aforesaid amine coupling technique may be performed in the same manner as that described above for the first embodiment.

How the fluorescence analysis apparatus 100-2A having the constitution described above operates will be described hereinbelow with reference to FIG. 6.

Firstly, the sensor section 151 is dipped in the blood plasma acting as the liquid sample. At this time, as illustrated in FIG. 6, the sensor section 151 is dipped in the liquid sample, such that the liquid surface of the liquid sample may be located at a height lower than the top end face of the cover section 153. In cases where the sensor section 151 is thus dipped in the liquid sample, the outside peripheral surface of the sensor section main body 152 comes into contact with the air atmosphere or the air layer A, and only the cover section 153 and the bottom end face 151a of the sensor section 151 come into direct contact with the blood plasma. Therefore, it is possible to prevent the problems from occurring in that the blood plasma is present at the outside peripheral surface of the sensor section main body 152, in which the exciting light and/or the received light is propagated. Also, in cases where the CRP antigen is contained in the blood plasma, the CRP antigen is bound with the primary antibody, which has been fixed on the bottom end face 151a of the sensor section 151. The sensor section 151 may be slightly moved up and down, while the sensor section 151 is being dipped in the blood plasma. In this manner, the binding of the CRP antigen and the primary antibody described above with each other is capable of being promoted.

Thereafter, the sensor section 151 is dipped in the reaction liquid, which contains the secondary antibody having been labeled with the fluorescent substance described above. At this time, in the same manner as that described above, the sensor section 151 is dipped in the reaction liquid, such that the liquid surface of the reaction liquid may be located at a height lower than the top end face of the cover section 153. In this state, the sensor section 151 is slightly moved up and down. In this manner, in cases where the CRP antigen has been bound with the primary antibody, which has been fixed on the bottom end face 151a of the sensor section 151, the binding of the CRP antigen and the secondary antibody described above with each other is capable of being promoted.

Thereafter, the sensor section 151 is dipped in the buffer liquid in the same manner as that described above and is moved up and down. In this manner, the bottom end face 151a of the sensor section 151 is washed with the buffer liquid. As a result, in cases where the aforesaid CRP antigen and the secondary antibody having been labeled with the fluorescent substance have been bound with each other, unnecessary matter other than the CRP antigen and the secondary antibody having been labeled with the fluorescent substance is washed off.

Thereafter, the fluorescence analysis is performed in the state, in which the sensor section 151 is being dipped in the buffer liquid in the same manner as that illustrated in FIG. 6. Specifically, at the time of the fluorescence analysis, the light source 150 is actuated to produce the exciting light 150a, such as the laser beam. The majority of the exciting light 150a travels downwardly in the guided mode within the sensor section main body 152, while the total reflection is being iterated at the interface between the peripheral surface of the sensor section main body 152 and the air atmosphere or the air layer A. The exciting light 150a, which has thus been propagated within the sensor section main body 152, reaches the bottom end face 151a of the sensor section 151 and is totally reflected from the bottom end face 151a of the sensor section 151. The values of the angle θ0, the diameter W, and the height H2 with respect to the sensor section main body 152 have been set in accordance with the refractive index n3 of the buffer liquid, such that the exciting light and/or the fluorescence may be totally reflected at the outside peripheral surface of the sensor section main body 152 and at the bottom end face 151a of the sensor section 151.

Also, at this time, the evanescent wave oozes out from the interface between the bottom end face 151a of the sensor section 151 and the buffer liquid. Therefore, in cases where the CRP antigen has been bound with the primary antibody on the bottom end face 151a of the sensor section 151, the secondary antibody contained in the reaction liquid is bound with the CRP antigen, and the fluorescent substance acting as the label of the secondary antibody is excited by the evanescent wave described above. The fluorescent substance having thus been excited by the evanescent wave produces fluorescence 159 having a predetermined wavelength. At least a part of the thus produced fluorescence 159 is propagated within the sensor section main body 152 and is reflected at a right angle from the dichroic mirror 122. The fluorescence 159 is thus detected by the photodetector 137.

In cases where the photodetector 137 detects the fluorescence 159 having the predetermined wavelength, it is possible to confirm that the secondary antibody has been bound with the CRP antigen, i.e. that the CRP antigen is contained in the blood plasma acting as the liquid sample. Also, in accordance with the intensity of a signal obtained from the detection of the fluorescence 159 described above, it is possible to detect the concentration of the substance to be analyzed. This embodiment of the fluorescence analysis apparatus 100-2A performs the fluorescence analysis in the manner described above.

As described above, with this embodiment of the fluorescence analysis apparatus 100-2A, the sensor section 151 is provided with the approximately cylindrical sensor section main body 152 and the cover section 153. Therefore, in cases where the sensor section 151 is dipped in the liquid sample such that the liquid surface of the liquid sample may be located at a position lower than the top end of the cover section 153, the cover section 153 comes into contact with the liquid sample. Also, in such cases, as for the sensor section main body 152, in which the exciting light and/or the received light is to be propagated, only the bottom end face 151*a*, i.e. the sensing part, of the sensor section main body 152, from which the evanescent wave is to be radiated out, comes into directly contact with the liquid sample. Therefore, it is possible to prevent the problems from occurring in that the outside peripheral surface of the sensor section main body 152 comes into direct contact with the liquid sample.

Therefore, with this embodiment of the fluorescence analysis apparatus 100-2A, the adverse effects of the absorption and the scattering of the exciting light and the fluorescence by the liquid sample are capable of being eliminated, and the analysis with respect to a trace amount of the substance to be analyzed is capable of being made with a sufficient accuracy. Also, with this embodiment of the fluorescence analysis apparatus 100-2A, wherein the outside peripheral surface of the sensor section main body 152 is not brought into contact with the liquid, such as the liquid sample, there is no risk that, as in cases where the fluorescence analysis is made in the state in which the sensor section 151 is dipped in the liquid, the total reflection conditions will alter in accordance with the technique for inserting the sensor section 151 into the liquid, the quantity of the liquid, sway of the liquid, and the like. Therefore, it is possible to keep good analysis reproducibility. Also, since the air layer A is capable of acting as a cladding layer, an optical fiber provided with a cladding layer, the cost of which optical fiber is high, need not be used for the sensor section 151. Therefore, the cost of the sensor section 151 is capable of being kept low.

In this embodiment of the fluorescence analysis apparatus 100-2A, the sensor section 151 is constituted such that the space between the outside peripheral surface 152*c* of the sensor section main body 152 and the cover section 153 is constituted of the air layer A. However, the fluorescence analysis apparatus in accordance with the present invention is not limited to the constitution of the sensor section 151 described above and may be modified in various other ways. For example, in cases where the analysis described above is to be performed in a vacuum, the space between the outside peripheral surface 152*c* of the sensor section main body 152 and the cover section 153 may constituted of a vacuum. Also, the end region on the side of the top end face of the cover section 153 may be blocked, and the space may be set in a vacuum.

Also, in this embodiment of the fluorescence analysis apparatus 100-2A, the dichroic mirror 122 is set such that the dichroic mirror 122 may transmit the light, which has a wavelength shorter than 645 nm, and may reflect the light, which has a wavelength longer than 645 nm, at a right angle. However, the fluorescence analysis apparatus in accordance with the present invention is not limited to the constitution described above. For example, alternatively, the dichroic mirror 122 may be set such that the dichroic mirror 122 may transmit the light, which has a wavelength longer than 645 nm, and may reflect the light, which has a wavelength shorter than 645 nm, at a right angle. In such cases, in the constitution illustrated in FIG. 6, the position of the set of the light source 150 and the optical system 121 and the position of the photodetector 137 may be reversed, such that the light having passed through the dichroic mirror 122 is capable of being detected by the photodetector 137.

Further, in this embodiment of the fluorescence analysis apparatus 100-2A, as the means for performing the fluorescence analysis, there is employed the so-called double path system, in which the photodetector 137 is located at the upside position, and in which the fluorescence 159 having been propagated within the sensor section main body 152 is detected by the photodetector 137. However, the fluorescence analysis apparatus in accordance with the present invention is not limited to the constitution described above. For example, as the means for performing the fluorescence analysis, it is also possible to employ the so-called single path system, in which the photodetector 137 is located at a downside position, and in which the fluorescence 159 having been produced by the fluorescent substance is directly detected by the photodetector 137.

Furthermore, in this embodiment of the fluorescence analysis apparatus 100-2A, the fluorescence analysis is performed in the state in which the sensor section 151 is being dipped in the buffer liquid. However, the fluorescence analysis apparatus in accordance with the present invention is not limited to the constitution described above. For example, alternatively, the fluorescence analysis may be performed in the state in which the sensor section 151 is being dipped in air or a liquid, such as the liquid sample or deionized water. In such cases, the same effects as those described above are capable of being obtained. In such cases, the sensor section 151 and the liquid described above are constituted such that the conditions for the exciting light 150*a* to be totally reflected from the bottom end face 151*a* of the sensor section 151 may be satisfied.

A fluorescence analysis apparatus 100-2B, which is a third embodiment of the fluorescence analysis apparatus in accordance with the present invention, will be described hereinbelow with reference to FIG. 8 and FIG. 9. FIG. 8 is a schematic side view showing the fluorescence analysis apparatus 100-2B. The fluorescence analysis apparatus 100-2B illustrated in FIG. 8 is constituted approximately in the same manner as that for the fluorescence analysis apparatus 100-1 illustrated in FIG. 1, except for the constitution of a sensor section 151-2. Therefore, in FIG. 8, similar elements are numbered with the same reference numerals with respect to FIG. 1. Accordingly, the explanation of the similar elements will hereinbelow be omitted.

The combination of the support base 31, the vertical member 32, and the vertical moving base 33 will hereinbelow be referred to as a support device. Also, the vertical moving base 33 is provided with the light source 150, which may be constituted of a semiconductor laser, or the like, for producing the exciting light 150*a* having a wavelength of, for example, 635 nm. The vertical moving base 33 is also provided with the chuck (acting as a support section) 49. The chuck 49 releasably supports the sensor section 151-2.

Figure 9:
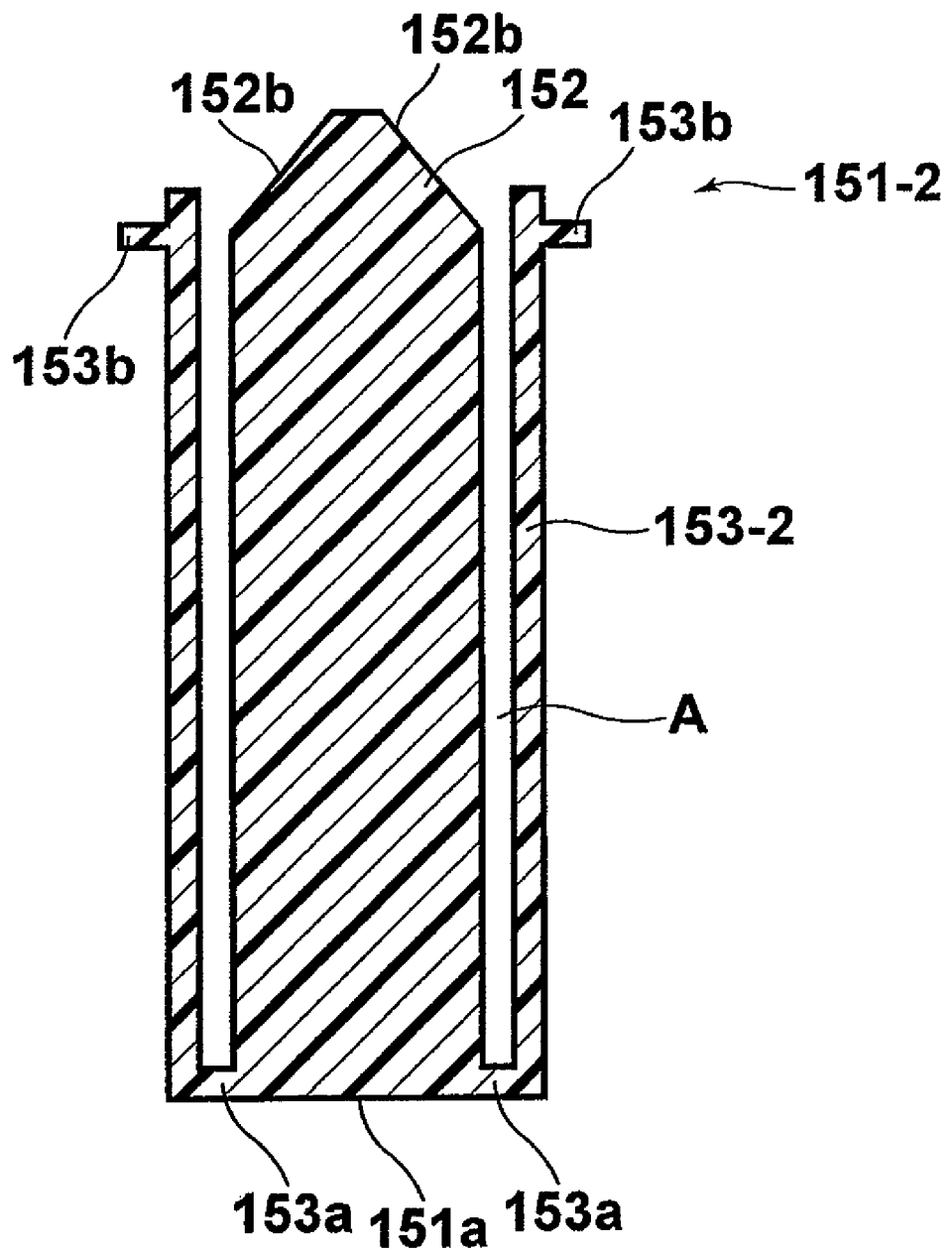
FIG. 9 is a sectional front view showing a sensor section in the fluorescence analysis apparatus of FIG. 8.

FIG. 9 is a sectional front view showing the sensor section 151-2 in this embodiment of the fluorescence analysis apparatus 100-2B of FIG. 8. In this embodiment, the sensor section 151-2 is constituted approximately in the same manner as that for the sensor section 151 employed in the embodiment illustrated in FIG. 6. Therefore, in FIG. 9, similar elements are numbered with the same reference numerals with respect to FIG. 6. Accordingly, the explanation of the similar elements will hereinbelow be omitted, and different features alone will be described hereinbelow.

In this embodiment of the fluorescence analysis apparatus 100-2B, the sensor section 151-2 is provided with a cover section 153-2, which has a shape different from the shape of the cover section 153 of the sensor section 151 employed in the embodiment of FIG. 6. Specifically, as illustrated in FIG. 9, the cover section 153-2 is provided with a plurality of engagement sections 153*b*, 153*b*, . . . , which have been formed at predetermined intervals for engagement with the chuck 49 described above. The plurality of the engagement sections 153b, 153b, . . . protrude in a pin-shaped form outwardly from the outside peripheral surface of the cover section 153-2 on the top end side of the cover section 153-2. By the provision of the plurality of the engagement sections 153b, 153b, . . . , the sensor section 151-2 is capable of being releasably fitted to the aforesaid chuck 49, i.e. to the aforesaid support device, in an easy manner without the optical path, and the like, being taken into consideration. Therefore, the sensor section 151-2 is capable of being easily located at the predetermined position. In this embodiment, as described above, the cover section 153-2 is provided with the plurality of the engagement sections 153b, 153b, . . . having the shape described above. However, the constitution of the cover section in the present invention is not limited to the constitution described above and may be altered appropriately in accordance with the shape of the chuck 49 of the support device, such that adverse effects may not be given to the optical path. The cover section 153-2 is formed with the depth of the hole region of the aforesaid turret 30, and the like, being taken into consideration such that, at the time at which the sensor section 151-2 is dipped in the liquid sample, the liquid surface of the liquid sample may be located at the height lower than the top end face of the cover section 153-2.

The steps of the fluorescence analysis performed by this embodiment of the fluorescence analysis apparatus 100-2B are approximately identical with the steps illustrated in FIGS. 3A to 3K. Therefore, the detailed explanation of the approximately identical steps will be omitted hereinbelow, and only the different operations will be described hereinbelow.

As illustrated in FIG. 3G, the sensor section 151-2 having been supported by the chuck 49 is slightly moved up and down in the state in which the sensor section 151-2 is being dipped in the blood plasma 58. In the same manner as that for the second embodiment described above, the dipping and the vertical movements of the sensor section 151-2 are performed such that the liquid surface of the blood plasma 58 may be located at the height lower than the top end face of the cover section 153-2. In this manner, the problems are prevented from occurring in that the blood plasma 58 clings to the outside peripheral surface of the sensor section main body 152. In cases where the sensor section 151-2 is thus moved up and down, if the CRP antigen is contained in the blood plasma 58, the binding of the CRP antigen and the primary antibody, which has been fixed to the bottom end face 151a of the sensor section 151-2, with each other will be promoted.

Also, as illustrated in FIG. 3H, the sensor section 151-2 having been supported by the chuck 49 is slightly moved up and down in the state in which the sensor section 151-2 is being dipped in the reaction liquid 45. In the same manner as that described above, the dipping and the vertical movements of the sensor section 151-2 are performed such that the liquid surface of the reaction liquid 45 may be located at the height lower than the top end face of the cover section 153-2. In this manner, the problems are prevented from occurring in that the reaction liquid 45 clings to the outside peripheral surface of the sensor section main body 152. In cases where the sensor section 151-2 is thus moved up and down, if the CRP antigen has been bound with the primary antibody on the bottom end face 151a of the sensor section 151-2, the binding of the CRP antigen and the secondary antibody, which is contained in the reaction liquid 45, with each other will be promoted.

With this embodiment of the fluorescence analysis apparatus 100-2B, the steps approximately identical with the steps illustrated in FIGS. 3A to 3I are performed. Thereafter, as illustrated in FIG. 3J, the through-hole 44 is located at the position just under the chuck 49. Thereafter, the chuck 49 is moved down, and the sensor section 151-2 is thus located within the through-hole 44. In this state, air alone is present around the sensor section 151-2. Therefore, the sensor section 151-2 is thus located in an atmosphere, which is substantially free from the occurrence of the absorption or the scattering of the exciting light and the fluorescence at the time of the fluorescence analysis described below.

The fluorescence analysis, which is performed in this state, will hereinbelow be described in detail with reference to FIG. 8, which illustrates the state described above. At the time of the fluorescence analysis, the light source 150 is actuated, and the exciting light 150a, such as the laser beam, is produced by the light source 150. The majority of the exciting light 150a travels downwardly in the guided mode within the sensor section main body 152, while the total reflection is being iterated at the interface between the outside peripheral surface of the sensor section main body 152 and air. A part of the exciting light 150a, which has thus been propagated within the sensor section main body 152, reaches the bottom end face 151a of the sensor section 151-2 and is totally reflected from the bottom end face 151a of the sensor section 151-2.

At this time, the evanescent wave oozes out from the interface between the bottom end face 151a of the sensor section 151-2 and air. Therefore, in cases where the CRP antigen has been bound with the primary antibody on the bottom end face 151a of the sensor section 151-2, the secondary antibody contained in the reaction liquid 45 described above is bound with the CRP antigen, and the fluorescent substance acting as the label of the secondary antibody is excited by the evanescent wave described above. The fluorescent substance having thus been excited by the evanescent wave produces the fluorescence 159 having the predetermined wavelength, and the thus produced fluorescence 159 is detected by the photodetector 137. In cases where the photodetector 137 detects the fluorescence 159 having the predetermined wavelength, it is possible to confirm that the secondary antibody has been bound with the CRP antigen, i.e. that the CRP antigen is contained in the aforesaid blood plasma 58 acting as the liquid sample. Also, in accordance with the intensity of a signal obtained from the detection of the fluorescence 159 described above, it is possible to detect the concentration of the substance to be analyzed.

When the fluorescence analysis has been finished in the manner described above, the sensor section 151-2 is pulled up from the through-hole 44, and the turret 30 is then rotated by a predetermined angle. In this manner, as illustrated in FIG. 3K, the sensor section support hole 43 is set at the position just under the chuck 49. Thereafter, the chuck 49 is moved down, and the sensor section 151-2 is thus inserted into the sensor section support hole 43. The chuck 49 is then opened and moved up, and the sensor section 151-2 is thus released from the chuck 49. In this manner, the sensor section 151-2 is returned into the sensor section support hole 43. Thereafter, the turret 30 having thus been used is scrapped, and a new turret 30 is set in the fluorescence analysis apparatus 100-2B. Therefore, the fluorescence analysis is capable of being performed without contamination being taken into consideration.

In this embodiment, as clear from the foregoing explanation, the sensor section actuating means is constituted of the turret 30, which acts as the rotating section, and the reciprocal movement means, which is provided with the vertical moving base 33 and the chuck 49. In cases where the turret 30 described above is used, the fluorescence analysis is capable of being performed markedly efficiently. However, the sensor section actuating means is not limited to the means described above and may be constituted of one of various other known mechanisms.

Also, in cases where contamination need not much be taken into consideration, the sensor section 151-2, or the like, may be washed, and a reagent may be loaded again. In this manner, it is possible to reuse the turret 30.

As described above, at the time at which the aforesaid fluorescence analysis is performed, the blood plasma 58 and the reaction liquid 45 do not cling to the outside peripheral surface of the sensor section main body 152. Therefore, the adverse effects of the absorption and the scattering of the exciting light 150a and the fluorescence 159 by the blood plasma 58 and the reaction liquid 45 are capable of being eliminated, and the analysis with respect to a trace amount of the substance to be analyzed is capable of being made with a sufficient accuracy. Further, at the time at which the aforesaid fluorescence analysis is performed, the sensor section 151-2 is located in the atmosphere, which is substantially free from the occurrence of the absorption or the scattering of the exciting light 150a and the fluorescence 159. Therefore, the problems are capable of being prevented from occurring in that the intensity of the fluorescence 159 detected becomes low due to the absorption or the scattering of the fluorescence 159, and in that the accuracy of the analysis of the substance to be analyzed is affected adversely. Also, the problems are capable of being prevented from occurring in that the exciting light 150a, such as the light having partially leaked out from the sensor section 151-2, is scattered and impinges upon the photodetector 37, and in that the analysis accuracy is thereby affected adversely.

Further, as described above, this embodiment of the fluorescence analysis apparatus 100-2B is provided the turret 30. However, the fluorescence analysis apparatus in accordance with the present invention is not limited to the provision of the turret 30. For example, alternatively, the fluorescence analysis apparatus in accordance with the present invention may be provided with a plurality of vessels. The constitution of the fluorescence analysis apparatus in accordance with the present invention may thus be modified in various other ways.

With the embodiments of the fluorescence analysis apparatus 100-2A and the fluorescence analysis apparatus 100-2B described above, the secondary antibody is detected from the fluorescence analysis, and the substance to be analyzed, which is contained in the liquid sample, is thus detected indirectly. However, the fluorescence analysis apparatus in accordance with the present invention is also capable of being constituted for directly detecting the substance to be analyzed, which is the fluorescent substance.

Figures 10A, 10B:
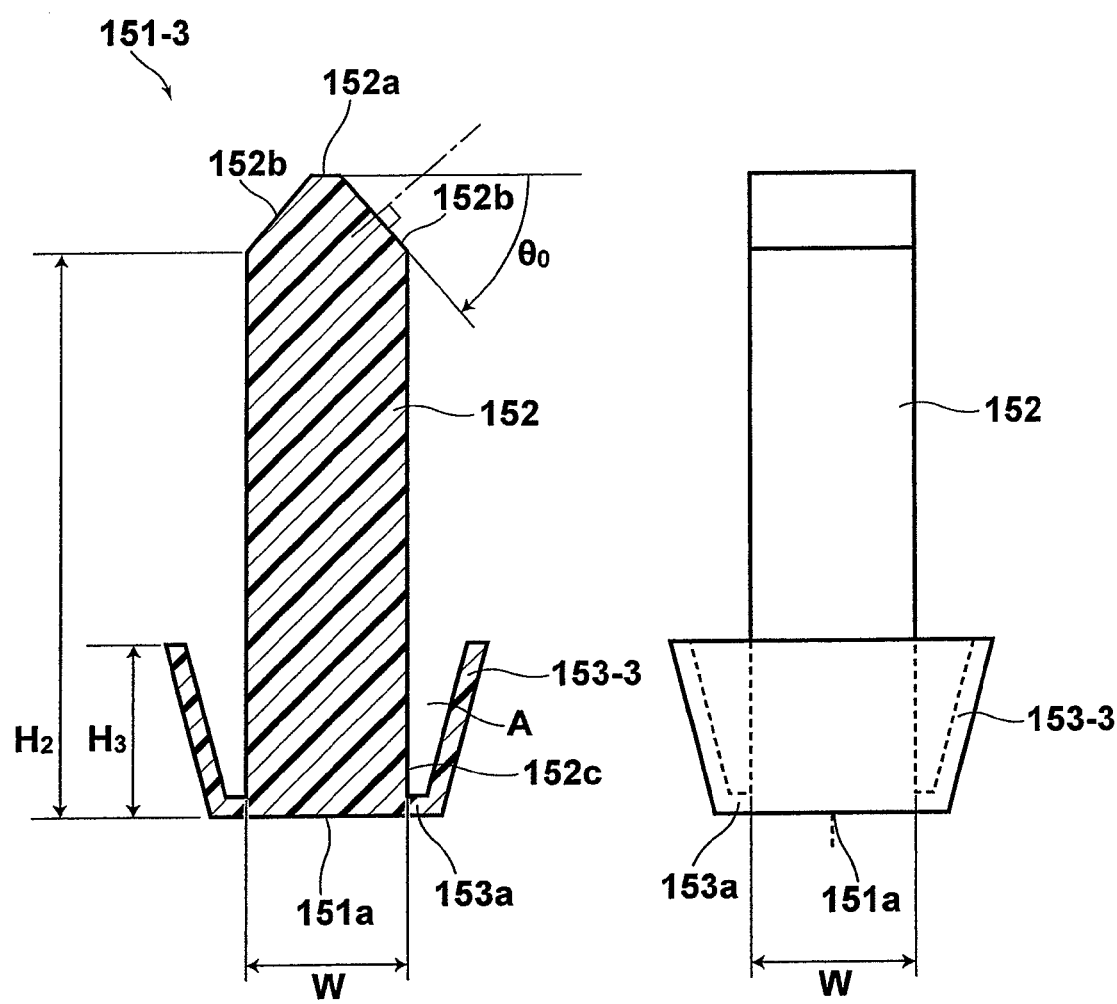
FIG. 10A is a sectional front view showing a sensor section in a fourth embodiment of the fluorescence analysis apparatus in accordance with the present invention.
FIG. 10B is a side view showing the sensor section of FIG. 10A.
Figure 11:
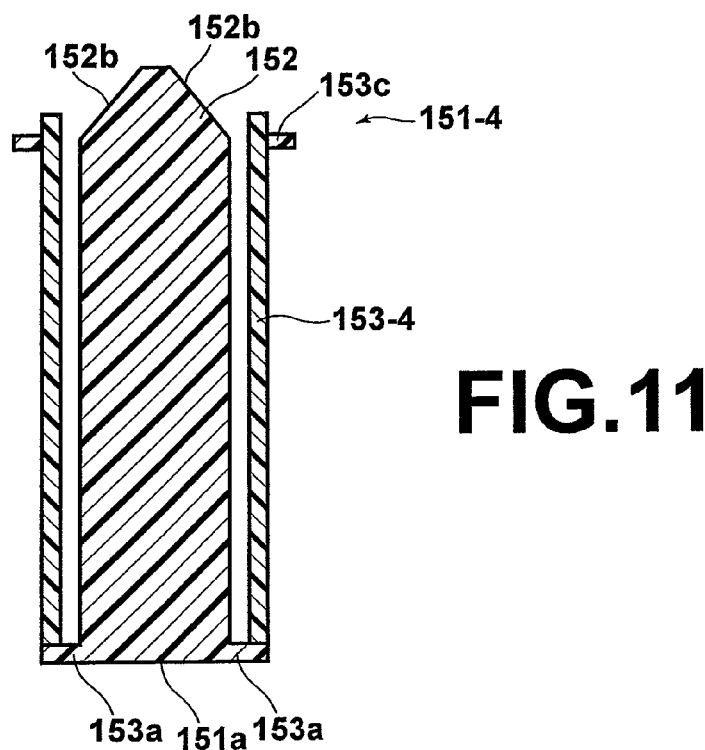
FIG. 11 is a sectional front view showing a sensor section in a fifth embodiment of the fluorescence analysis apparatus in accordance with the present invention.
Figure 12A:
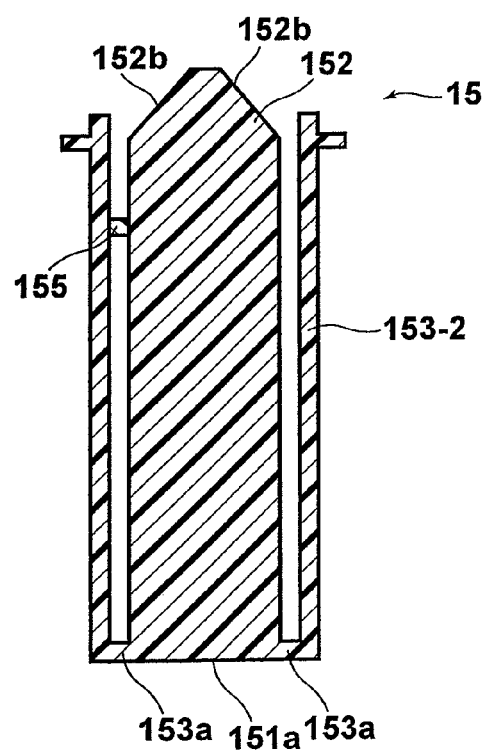
FIG. 12A is a sectional front view showing a sensor section in a sixth embodiment of the fluorescence analysis apparatus in accordance with the present invention.
Figure 12B:
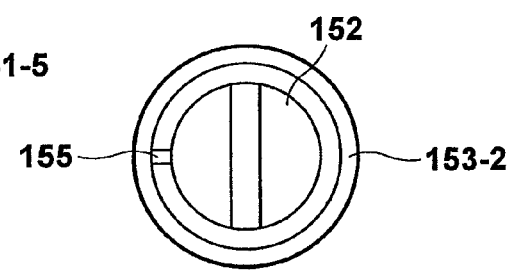
FIG. 12B is a top plan view showing the sensor section of FIG. 12A.

Also, the sensor section constituting the second fluorescence analysis apparatus in accordance with the present invention is not limited to the aforesaid sensor section 151 illustrated in FIG. 6 and the aforesaid sensor section 151-2 illustrated in FIG. 8 and may be modified in various other ways. Various modifications of the sensor section constituting the second fluorescence analysis apparatus in accordance with the present invention will be described hereinbelow. FIG. 10A is a sectional front view showing a sensor section 151-3 in a fourth embodiment of the fluorescence analysis apparatus in accordance with the present invention. FIG. 10B is a side view showing the sensor section 151-3 of FIG. 10A. FIG. 11 is a sectional front view showing a sensor section 151-4 in a fifth embodiment of the fluorescence analysis apparatus in accordance with the present invention. FIG. 12A is a sectional front view showing a sensor section 151-5 in a sixth embodiment of the fluorescence analysis apparatus in accordance with the present invention. FIG. 12B is a top plan view showing the sensor section 151-5 of FIG. 12A.

The sensor section 151-3 in the fourth embodiment of the fluorescence analysis apparatus in accordance with the present invention is constituted approximately in the same manner as that for the sensor section 151 in the second embodiment illustrated in FIG. 6, except for the shape of a cover section 153-3. As illustrated in FIGS. 10A and 10B, the sensor section 151-3 in the fourth embodiment is formed in a tubular shape, the diameter of which becomes large from the bottom end toward the top end. The sensor section 151-3 constituted in this manner is advantageous in that the sensor section 151-3 is capable of being easily drawn out from a mold at the time of the integral molding processing.

The sensor section 151-4 in the fifth embodiment of the fluorescence analysis apparatus in accordance with the present invention has the same shape as that of the sensor section 151-2 in the third embodiment illustrated in FIG. 8, except that, as illustrated in FIG. 11, a cover section 153-4 is formed with molding processing from a material, which is capable of absorbing the exciting light 150a and/or the fluorescence 159. Examples of the materials, which are capable of absorbing the exciting light 150a and/or the fluorescence 159, include a molding material, which is employed in a plastic filter (PIR730 or PIR800, supplied by Yasunaka Special Glass Mfg. Co., Ltd.), and a mixture of a polycarbonate (PC) or a polyethersulfone (PES) with an ordinary azo dye or other various dyes. Also, the sensor section main body 152 and the cover section 153-4 of the sensor section 151-4 are formed with integral molding processing utilizing a two-color molding technique. In cases where the cover section 153-4 is thus formed with the molding processing from the material, which is capable of absorbing the exciting light 150a and/or the fluorescence 159, the cover section 153-4 is capable of absorbing, for example, the scattered light, which is caused to occur in cases where, for example, the exciting light 150a and/or the fluorescence 159 is scattered by impurities contained in the sensor section main body 152, and the like. Therefore, the problems are capable of being prevented from occurring in that the scattered light described above is detected by the photodetector 37. In this embodiment, as described above, the cover section 153-4 is formed with the molding processing from the material described above. However, the fluorescence analysis apparatus in accordance with the present invention is not limited to the formation of the cover section 153-4 with the molding processing. For example, alternatively, the cover section may be coated with the material, which is capable of absorbing the exciting light 150a and/or the fluorescence 159.

The sensor section 151-5 in the sixth embodiment of the fluorescence analysis apparatus in accordance with the present invention is constituted approximately in the same manner as that for the sensor section 151-2 in the third embodiment illustrated in FIG. 8, except that, as illustrated in FIGS. 12A and 12B, a rib 155 for reinforcement is formed at a part of the sensor section main body 152, at which part the exciting light 150a is not reflected totally, such that the rib 155 may form a bridge between the part of the sensor section main body 152, at which part the exciting light 150a is not reflected totally, and the cover section 153-2. In cases where the rib 155 is thus provided, the intensity of the cover section 153-2 is capable of being reinforced. In this embodiment, only one rib 155 is provided. However, the fluorescent analysis apparatus in accordance with the present invention is not limited to the constitution described above. For example, alternatively, a plurality of ribs may be located at predetermined intervals along the peripheral direction. As another alternative, a plurality of ribs may be located along the vertical direction. The plurality of the ribs may thus be located at various positions, at which the exciting light 150a is not reflected totally.

A height H of the position, at which the exciting light 150a is reflected totally, is capable of being calculated from the internal reflection angle $\theta1$ as illustrated in FIG. 6 and the diameter W of the sensor section main body 152 by use of the formula $H=n\times(W/2)\tan\theta1$, wherein n represents an odd integral number. At the position of the height H described above, the exciting light 150a is reflected totally. Therefore, the position, at which the exciting light 150a is not reflected totally, is the position at the height different from the height H of the position, at which the exciting light 150a is reflected totally, the height H being calculated with the formula shown above. For example, in cases where W=10 mm, $\theta1=37$ degrees, and n=7, the height H of the position, at which the exciting light 150a is reflected totally, is calculated as $H=7\times(10/2)\tan 37o=26.3$ mm. Also, in cases where n=5, the aforesaid height H is calculated as H=18.8 mm. Therefore, the position, at which the exciting light 150a is not reflected totally, is the position at the height falling within the range of the height H=18.8 mm to 26.3 mm. Accordingly, the rib 155 is capable of being formed at the position of, for example, the height H=22.56 mm, which is the intermediate height value of the range described above.

The fluorescence analysis apparatus in accordance with the present invention is not limited to the embodiments described above and may be embodied in various other ways.

What is claimed is:

1. A fluorescence analysis apparatus, comprising:
i) a light source for producing exciting light,
ii) a sensor section for propagating the exciting light through the interior of the sensor section to radiate out the thus propagated exciting light from an outside surface of the sensor section, such that the exciting light having thus been radiated out may excite a fluorescent substance for indicating the presence of a substance to be analyzed in a liquid sample;
iii) a photodetector for detecting the fluorescence, which has been produced by the fluorescent substance when the fluorescent substance is excited by the exciting light;
iv) sensor section actuating means for dipping the sensor section in the liquid sample, and thereafter moving the sensor section into a predetermined atmosphere, which is substantially free from occurrence of absorption or scattering of the exciting light and the fluorescence;
v) control means for actuating the light source and the photodetector in a state, in which the sensor section has been located in the predetermined atmosphere, and thereby causing a fluorescence detecting operation to be performed.

2. An apparatus as defined in claim 1 wherein the sensor section propagates the exciting light in a guided mode, such that an evanescent wave may ooze out from the outside surface of the sensor section and may excite the fluorescent substance.

3. An apparatus as defined in claim 1 wherein the predetermined atmosphere is air.

4. An apparatus as defined in claim 1 wherein the predetermined atmosphere is a buffer liquid.

5. An apparatus as defined in claim 1 wherein the predetermined atmosphere is an atmosphere, which does not contain the liquid sample and the fluorescent substance that acts as a label.

6. An apparatus as defined in claim 1 wherein the sensor section actuating means is constituted of:
a rotating section, which is provided with at least a region for retaining the liquid sample, and a region for retaining the predetermined atmosphere, and which is capable of being rotated such that the region for retaining the liquid sample and the region for retaining the predetermined atmosphere may be successively kept stationary at a predetermined position, and
reciprocal movement means for introducing the sensor section into the liquid sample at the time, at which the rotating section is kept stationary and at which the liquid sample has been located at the predetermined position, and for introducing the sensor section into the predetermined atmosphere at the time, at which the rotating section is kept stationary and at which the predetermined atmosphere has been located at the predetermined position.

7. An apparatus as defined in claim 1 wherein the apparatus further comprises a reaction vessel for retaining a liquid containing an antibody, which has been labeled with the fluorescent substance and which is capable of undergoing binding with an antigen acting as the substance to be analyzed in the liquid sample, and
the sensor section actuating means is constituted such that, after the sensor section actuating means has dipped the sensor section in the liquid sample, the sensor section actuating means dips the sensor section in the liquid retained in the reaction vessel and thereafter moves the sensor section into the predetermined atmosphere.

8. A fluorescence analysis apparatus, comprising:
i) a light source for producing exciting light,
ii) a sensor section for propagating the exciting light, which has entered into the sensor section from one end of the sensor section, through the interior of the sensor section to radiate out an evanescent wave from the other end of the sensor section, such that the exciting light may excite a fluorescent substance for indicating the presence of a substance to be analyzed in a liquid sample, in which the other end of the sensor section is dipped;
iii) a photodetector for detecting the fluorescence, which has been produced by the fluorescent substance when the fluorescent substance is excited by the exciting light;
iv) an approximately cylindrical sensor section main body; and
v) a tubular cover section for surrounding the sensor section main body, such that space may intervene between the cover section and an outside peripheral surface of the sensor section main body, which outside peripheral surface is adjacent at least to the other end of the sensor section,
the cover section being provided with a blocking section for blocking the space, which intervenes between the cover section and the outside peripheral surface of the sensor section main body, at an end of the cover section, which end is located on the side of the other end of the sensor section.

9. An apparatus as defined in claim 8 wherein a rib for reinforcement is formed at a part of the sensor section main body, at which part the exciting light is not reflected, such that the rib may form a bridge between the part of the sensor section main body, at which part the exciting light is not reflected, and the cover section.

10. An apparatus as defined in claim 8 wherein the cover section is molded or coated with a material, which is capable of absorbing the exciting light and/or the fluorescence.

11. An apparatus as defined in claim 8 wherein the cover section is formed with integral molding processing together with the sensor section main body.

12. An apparatus as defined in claim 8 wherein the cover section is provided with an engagement section for engaging with a support section of a support device, which supports the sensor section at a predetermined position.

13. An apparatus as defined in claim 8 wherein the sensor section main body propagates the exciting light in a guided mode.

14. An apparatus as defined in claim 8 wherein a ligand, which is capable of undergoing specific binding with the substance to be analyzed, is fixed to an outside surface of the other end of the sensor section.

* * * * *